US012629048B2

(12) United States Patent
Ganesan et al.

(10) Patent No.: US 12,629,048 B2
(45) Date of Patent: May 19, 2026

(54) STRUCTURE MASKING OR UNMASKING FOR OPTIMIZED DEVICE-TO-IMAGE REGISTRATION

(71) Applicant: CANON U.S.A., INC., Melville, NY (US)

(72) Inventors: Santosh Narayan Ganesan, Cambridge, MA (US); Antonio Bonillas Vaca, Boston, MA (US)

(73) Assignee: CANON U.S.A., INC., Melville, NY (US)

( * ) Notice: Subject to any disclaimer, the term of this patent is extended or adjusted under 35 U.S.C. 154(b) by 0 days.

(21) Appl. No.: 18/673,046

(22) Filed: May 23, 2024

(65) Prior Publication Data

US 2024/0306931 A1     Sep. 19, 2024

Related U.S. Application Data

(63) Continuation of application No. 16/566,551, filed on Sep. 10, 2019, now Pat. No. 12,023,143.

(Continued)

(51) Int. Cl.

| | |
|---|---|
| *A61B 5/06* | (2006.01) |
| *A61B 90/00* | (2016.01) |
| *A61B 90/11* | (2016.01) |
| *G06T 5/75* | (2024.01) |
| *G06T 7/33* | (2017.01) |

(52) U.S. Cl.
CPC .............. *A61B 5/064* (2013.01); *A61B 90/11* (2016.02); *A61B 90/39* (2016.02); *G06T 5/75* (2024.01); *G06T 7/337* (2017.01); *A61B*

*2090/3983* (2016.02); *G06T 2207/20092* (2013.01); *G06T 2207/30004* (2013.01);
(Continued)

(58) Field of Classification Search
None
See application file for complete search history.

(56) References Cited

U.S. PATENT DOCUMENTS

| | | | |
|---|---|---|---|
| 2013/0127915 A1* | 5/2013 | Gilra .................... | H04N 1/3875 |
| | | | 345/660 |
| 2014/0275979 A1* | 9/2014 | Fujimoto ........... | A61B 17/3403 |
| | | | 600/410 |

(Continued)

*Primary Examiner* — Patricia J Park
(74) *Attorney, Agent, or Firm* — CANON U.S.A., INC. IP DIVISION

(57) ABSTRACT

One or more devices, systems, methods and storage mediums for performing medical procedure (e.g., needle guidance, ablation, biopsy, etc.) planning and/or performance, and/or for performing registration using at least one mask, are provided. Examples of applications for such devices, systems, methods and storage mediums include imaging, evaluating and diagnosing biological objects, such as, but not limited to, lesions and tumors, and such devices, systems, methods and storage mediums may be used for radiotherapy applications (e.g., to determine whether to place seed(s) for radiotherapy). The devices, systems, methods and storage mediums provide improved registration results by utilizing at least one mask to suppress one or more artifacts or objects (which may or may not include, but is not limited to, at least one medical instrument or tool) in an image including a portion of the medical guidance device and/or to enhance a region or target of interest in the image.

16 Claims, 17 Drawing Sheets

Related U.S. Application Data

(60) Provisional application No. 62/747,895, filed on Oct. 19, 2018.

(52) U.S. Cl.
CPC ............... *G06T 2207/30196* (2013.01); *G06T 2207/30204* (2013.01); *G06T 2207/30241* (2013.01)

(56) References Cited

U.S. PATENT DOCUMENTS

| | | | |
|---|---|---|---|
| 2017/0000581 A1* | 1/2017 | Tokuda | G06V 10/40 |
| 2017/0196535 A1* | 7/2017 | Arai | A61B 8/466 |
| 2019/0000372 A1* | 1/2019 | Gullotti | A61B 90/39 |
| 2021/0137605 A1* | 5/2021 | Samadani | G16H 40/63 |
| 2021/0142504 A1* | 5/2021 | Dascal | G06T 7/0012 |

* cited by examiner

STRUCTURE MASKING OR UNMASKING FOR OPTIMIZED DEVICE-TO-IMAGE REGISTRATION

CROSS-REFERENCE TO RELATED APPLICATION(S)

This application is a continuation, and claims the benefit, of U.S. patent application Ser. No. 16/566,551, presently pending and filed on Sep. 10, 2019, which relates, and claims priority, to U.S. Patent Application Ser. No. 62/747, 895, filed Oct. 19, 2018, the entire disclosures of which applications are incorporated by reference herein in their entireties.

FIELD OF THE DISCLOSURE

The present disclosure relates generally to the field of imaging, such as, but not limited to, in the field of interventional oncology, and more particularly to apparatuses, systems, methods and storage mediums for guidance of one or more medical instruments, such as needles used for minimally invasive puncture treatment, and for structure masking for improved or optimized device-to-image registration of such guidance apparatuses, systems, methods, and storage mediums. Examples of medical applications include, but are not limited to, imaging, evaluating and characterizing/identifying biological objects or tissue, such as, but not limited to, for identification, location and treatment of lesions/tumors, operation/procedure planning, simulation, ablation performance, biopsy performance, guiding needles or probes and visualization, manipulation and registration of guidance devices or systems.

BACKGROUND

Minimally invasive medical procedures are becoming increasingly popular in the medical community due to shortened hospital stays and improved quality of life for the patient. For example, in the field of interventional oncology, percutaneous ablations are often preferred over surgical resection due to the minimally invasive nature of the procedure and thus shortened patient recovery period.

There are various forms of ablation, and successful ablation requires good planning. Ablation is normally ordered after diagnosis by oncologists who decide the ablation procedure is the best to treat a lesion/tumor. An interventional radiologist (IR) may be involved to gather and analyze images to accurately characterize tumors and their size and to review results from a biopsy procedure. However, diagnostic imaging is rarely good enough to plan with, so an IR may conduct initial imaging before developing/finalizing an action plan and starting an ablation procedure. The ablation strategy may include selection of an imaging modality in the procedure, probe insertion points, a number of probes and trajectories of the insertion, a modality of ablation such as microwave, cryo, etc., patient position during the procedure, coordinating with other clinicians (e.g., anesthetist, nurses, equipment technicians, etc.), etc.

Ablation takes a lot of planning, and there are a lot of variables. For example, clinicians in ablation planning try to figure out where is the target ablation zone including a lesion/tumor, where are the critical structures/features that must be avoided during the procedure, where is the target point in the target zone, what is the entry point on the body surface so that the probe can get into the body and reach a target point(s), what is the trajectory to connect an entry point to a target point while avoiding any critical structure/ feature with consideration of needle orientation when scanning the body with the needle inserted, how many probes are needed to form an ablation zone, how big and what shape the ablation zone is, etc. When a lesion/tumor is identified and an ablation zone is defined, based on ablation probe type and quantities, clinicians normally use a visual overlay of the two zones to estimate the coverage zone, which tends to be inaccurate or be a less objective measure since it is a mental visual estimate.

Even though medical procedures (e.g., ablation, biopsy, needle guidance, etc.) are very complex, the procedure that is currently performed by clinicians is predominantly done manually and iteratively, which is error prone and may increase the time required to perform, for example, an ablation (i.e., be inefficient). Planning in particular is largely performed by clinicians with some help from basic visualization software. Clinicians typically start with reading Computed Tomography (CT) or Magnetic Resonance Imaging (MRI) scans, identify the target region and plan the insertion point and/or trajectory/orientation. For example, in at least one ablation planning scenario, clinicians load Digital Imaging and Communications in Medicine (DICOM) images of a patient into a computer and view 2D slice by slice of the CT or MRI scans of the patient. By going through the DICOM image slices, a clinician may construct a mental 3D model of internal anatomy of concern. By using the DICOM images, the clinicians may identify where the lesion/tumor is and may identify the relationship of the lesion/tumor and its surrounding critical structure, to determine the optimal probe entry point, target point and consequently the trajectory from the entry point to the target point.

During an image guided surgical procedure, an instrument such as a needle guidance device is manipulated relative to a patient. Medical images, such as CT images, MRI images, etc., may be used to plan the procedure, but the position of the instrument relative to the imaged anatomy must be determined to inform the surgical procedure. A registration or translation map must be generated to correlate the patient space, device space, and image space. In many applications in the medical field, accurate and precise positioning of medical instruments is critical. In the case of surgical procedures such as percutaneous intervention, exact placement of needle-like medical tools and instruments can mean the difference between success and failure of procedures.

Registration of patient, device, and image space may be performed. However, it is often difficult for the user to quickly and easily visualize and manipulate the results of registration.

Once a medical device, such as a guidance device, is registered and positioned on a patient or over a target area of a body of the patient, the clinicians may identify the entry point on the surface of the body that corresponds to what the clinicians envisioned in the image scans. The clinicians may perform a test drive to insert a needle a little bit, perform a scan, and find the difference between the actual needle insertion demonstrated by the scan and what was expected before the insertion. This gives the clinicians a chance to make any correction if necessary. This step may be repeated several times for the needle to finally reach the target point.

Typically, where the medical procedure is ablation, a target point is in a center of the lesion/tumor in a case where a single probe is used. Clinicians may use a pointing device such as a mouse or touch point to mark a location in the center of the lesion/tumor which is shown in the basic visualization software. Clinicians may either place a probe tip to allow ablation to occur, or may implant seeds for radio/chemo therapy. Even the marking process is manual and approximate in nature. In 2D, marking a center position for an object may not be hard, even though many times it may not be accurate due to human visual and motor action inaccuracy/error. However, a clinician using 2D slice view to figure out a center of a 3D volume which includes a stack of 2D slices may be difficult and error prone if the center of the volume is the target point, and the clinician may be tricked by image artifacts and/or human limitation in 3D reasoning. In 3D, marking a center position is much harder because of the intricate limitation of visualization/rendering software. Relying on clinicians' intuition, experience and visual understanding to define a target point is not optimal (for reliability, repeatability, traceability, etc.), particularly in 3D space. When the lesion/tumor has a very complicated shape, defining an appropriate target is more or less an art, and it is difficult to achieve consistency.

If multiple needles are needed to make the ablation zone large enough to cover the target zone, clinicians typically use a first needle as reference, and plan the next needles based on the result from the first or previous needle insertion and/or ablation. If there are multiple needle insertions needed, cases are done mostly in an incremental fashion—for example, plan, insert a needle, scan, make an adjustment or modification to the original plan (if needed) based on the scan of the inserted needle, insert another needle, etc.

Devices/hardware is also lacking to help clinicians aid in the insertion of multiple probes or needles and in the registration of such guidance devices, probes and/or needles during a procedure, such as, but not limited to ablation, biopsy, or other procedures.

In current practice, as aforementioned, needles or other devices, such as ablation probes, are guided in a free-handed manner using medical imaging for guidance. It is very difficult to achieve these preset needle or probe configurations with this approach and thus an improved guidance, visualization and/or registration method is needed. Clinicians employ incremental insertion movement by trial and error to deal with the inevitable organ movement and deformation (e.g., as aforementioned, a clinician may insert a needle a little, scan, read the image(s) to find out how much the needle is off, adjust or change the needle trajectory if needed or keep going, if the target point is moved during probe insertion, etc.). Currently, a first probe insertion is made and scanned to use the scan as a reference. Then subsequent incremental insertions of the probe may be made towards the target with scans after each insertion to assess same. Such a process may include repositioning the patient if needed to make insertion more controllable. Additionally, an IR or clinician may assume the probe is rigid and that organs have no deformation and movement from now until the insertion. Alternatively to scanning, an ultrasound transducer along with the ablation probe may be used to guide the probe into the planning direction to reach the target, which requires ultrasound image fusion with CT/MRI (CT fluoroscopy is another technique that may be used with CT during planning and performance of ablation). This not only increases the procedure time, but also wastes a lot of efforts in adjustment/making changes. Of course, it is also likely having impact(s) on or causing possible damage to nearby structure and tissues. Considering organ movement and deformation may make medical procedure planning and performance more complex, and may hamper interaction between clinicians and ablation planning and performance devices. The reality is that many factors (e.g., breathing, body movement or pose change, organ deformation due to interaction with the probe, etc.) affect probe insertion and may change between planned insertion and actual insertion. Such changes may also invalidate the planned insertion. Respiratory gating, or asking patients to hold their breath, is time consuming monitoring techniques that may be used to assist with insertion. Modeling organ deformation is another way to try to anticipate movement and deformation issues with insertion. However, such procedures do not guarantee success or efficiency. Ultimately, the purpose of probe registration and insertion is to perform or conduct a medical procedure (e.g., biopsy, ablation, etc.), and procedures are needed to reduce and/or avoid the aforementioned issues with needle insertion. Once the needle or probe is setup properly, the procedure is thereafter performed.

Additionally, noise may exist in a region of interest, which interferes with device-to-image registration.

In situations dependent on the type of medical images being obtained, a user of a guidance device may have to address different issues. For example, in MRI, a user may select a limited rectangular field-of-view (FOV) which may only encompass the device in which to register and which may limit the image volume to search for fiducials. As another example, CT may not have as much flexibility in setting an imaging FOV (e.g., may be 50 cm); it may not be possible to restrict imaging to the location of the interventional instrument guidance device in CT, which prevents achieving accurate and robust fiducial detection and device restriction due to other high intensity image features, which may be mistakenly detected as fiducials (e.g., metal in a patient bed or support structure, metal in padding underneath the patient, dense anatomical structures such as bone, a needle, an accessory cable, etc.). Detection of such inaccurate features as fiducials (in other words, detecting false positives; also referred to herein as misdetection) causes such registration to fail or be deficient.

In view of the above, there is a need for software and/or hardware to provide clinicians with help to make visualization, manipulation and registration more efficient (e.g., reduce procedure time), more accurate, and more effective (including, but not limited to, more cost-effective (cheaper), optimized for lesion/tumor removal, etc.), in addition to providing enhancement in visualization, manipulation and/or needle or probe guidance/placement. There is a need for an intuitive way to reduce and/or eliminate noise that may exist in a region of interest to improve or optimize device-to-image registration and to reduce or eliminate registration error. There is a need to prevent or avoid misdetection of features in an image as being considered a fiducial, and there is a need to improve or optimize registration by avoiding such false positives.

SUMMARY

One or more systems, devices, methods and storage mediums are provided herein, including, but not limited to, apparatus(es), system(s) or device(s), and methods and storage mediums for guiding multiple needles or ablation probes and/or for performing structure masking to improve or optimize device-to-image registration. In the medical environment, in one or more applications, it is necessary to position a needle or multiple needles, or a probe or multiple probes, precisely inside and/or on tissue or a specific organ for accurate diagnosis or minimally invasive procedure(s), such as, but not limited to, therapy, treatment, etc.

One or more embodiments of the present disclosure relate to one or more medical devices, methods and storage mediums for holding and positioning a needle or needles, or a probe or multiple ablation probes, in desired geometric configurations and/or for performing structure masking to improve or optimize a device to image registration (also referred to herein as device-to-image registration) algorithm.

One or more embodiments provide useful hardware for physically guiding planned needles along planned trajectories, and/or for performing structure masking to improve or optimize a device-to-image registration. Masking allows for more reliable device-to-image registration in instances where there is noise within the region of interest. Cropping alone does not account for such scenarios.

Preferably, detecting high intensity fiducials in medical images (CT, MRI, etc.) for device-to-image registration (e.g., automatic or manual registration) is used in one or more embodiments for interventional instrument guidance devices. Masking predetermined or certain detected features, in situations where such features are determined to be false positives or are misdetected as fiducials, can help improve or optimize device-to-image registration (e.g., automatic or manual registration).

One or more embodiments of the present disclosure utilize pre-procedure planning, which encompasses the selection of the insertion and target points, to automatically mask the desired area of acquired images in order to increase the accuracy of device-to-image registration. At least one goal is to have a high registration accuracy over more diverse data sets which may include noise within the region of interest (e.g., from needle artifacts, electronic components, metal components in padding, a patient support structure (e.g., a bed), cabling, etc.). In some of these cases, this type of noise may be mistaken for the detection of fiducials. One or more embodiments operate to use masking of artifacts to prevent or reduce such misdetection.

In one or more embodiments, masking may be part of a multiple needle guided scenario with several planned trajectories, where the increased probability exists of missed fiducial detection or misdetection. In this circumstance, masking may also be selectively turned on and off to help the physician highlight the needle of interest within the CT image or other medical image.

More or more embodiments employ a technique of enhancing structures. For example, in certain instances, noisy medical images (e.g., noisy CT images) may be obscured by the imaging device (e.g., the CT). In such an environment, masking may be used to enhance desired areas in noisy images alone or in addition to using masking for suppression of artifacts.

One or more embodiments are used in an environment which tries to match a model or a device plane of known fiducial orientation with an image containing fiducials. Subsequently, such planes may be overlaid and registered. However, as aforementioned, noise may be introduced within such a registration process, due to artifacts or noise in the image.

In at least one embodiment, at least one method for performing device-to-image registration involves masking one or more artifacts to suppress any negative impact of the one or more artifacts on the registration process.

In at least one embodiment, at least one additional method for performing device-to-image registration involves masking using one or more needle dimensions to suppress any negative impact of the one or more needles on the registration process.

In at least one embodiment, at least another method for performing device-to-image registration involves masking multiple needles except for a target needle to suppress any negative impact of the one or more other needles on the registration process.

Additionally or alternatively, in at least one further embodiment of a method for performing device-to-image registration may involve masking to enhance regions of interest in an image when performing device-to-image registration to improve or optimize placement of the needle(s) and/or probe(s).

In one or more embodiments, percutaneous ablation procedures involve the physician having to guide ablation probe(s) to a target of interest, such as an area of interest (e.g., a tumor, a nodule, a lesion, etc.), deep in the body with the aid of medical imaging (e.g., CT, MRI, Ultrasound, other scanning devices, etc.). For example, various ablation modalities exist (radiofrequency, microwave, cryo, laser, and irreversible electroporation). The physician selects the needle(s) or probe(s) which will be able to perform a desired medical procedure (e.g., fully ablate a tumor along with a safety margin surrounding the tumor to reduce the risk of tumor recurrence). In some cases, a single needle or probe may not be enough to achieve the desired procedure (such as, but not limited to, achieve full tumor coverage), and thus multiple needles or probes may be used (e.g., for a larger ablation zone to ensure full tumor coverage). Moreover, there is often a preset probe configuration that is desired in each ablation modality. For example, in microwave and irreversible electroporation a parallel probe configuration is desired. In the parallel probe configuration, probes are guided parallel at a preset maximum distance. The preset maximum distance ensures a larger uniform ablation zone. Exceeding the maximum probe distance may result in independent ablation zones around each probe and thus lead to missed tumor cells between probes causing or leading to tumor recurrence. In cryo-ablation, many physicians prefer to bracket the tumor in a conical probe arrangement in order to ensure all insertion points of the probes are in close proximity. Sharing a close insertion point for all probes in cryo-ablation is desired so that the physician can more easily protect the skin from cryo burns by applying warm saline around the probe insertion points. In one or more embodiments, drug delivery and/or treatment may also be performed in addition to one or more of biopsy, ablation, therapy (e.g., cryotherapy), aspiration, etc. One or more embodiments of the present disclosure provide configurations and processes for achieving guidance and placement of needle(s) and/or probe(s) to perform a desired minimally invasive procedure(s), including using one or more methods for masking artifact(s) or needle(s) (e.g., one or more needles; needles that are not the target needle, etc.) to suppress such items during registration, or for masking to enhance regions of interest in an image when performing device-to-image registration to improve or optimize placement of the needle(s) and/or probe(s).

In one or more embodiments, an apparatus and a method for a medical guidance device may include a base assembly including a base ring or a fixed portion having an inner circumference defining an opening, and a guide or moving portion rotatably mateable with the base assembly, the guide having a frame with an inner circumference defining an opening and an outer circumference, wherein, in a configuration where the guide is mated with the base assembly, the opening of the frame overlays the opening of the base ring. The medical guidance apparatus also has an arc member (and may, in one or more embodiments, have a holder slideably attached to the arc member, wherein the holder is configured to hold a medical tool intended to be guided by the medical guidance apparatus). Preferably, in one or more embodiments, the fiducial markers are located or disposed in the base assembly (e.g., in a base ring or fixed portion, portion attached to a patient, in the rotatably mateable guide or moveable portion, etc.).

In one or more embodiments, the arc member comprises a guidance surface, wherein the guidance surface comprises one or more angular reference marks. The angular reference marks may be used to align with an indicator configured upon the arc member guidance surface to accurately situate the holder in the desired angular position (especially after the guide device is registered). In further embodiments, the medical guidance apparatus comprises a gap extending from the inner circumference of the frame to the outer circumference of the frame, to allow for detachment and/or reattachment of the medical guidance apparatus to the surface without interrupting the medical tool.

In additional embodiments, the holder further comprises a groove for accepting the medical tool and a door for holding the medical tool in the holder. Furthermore, the door may be hingedly attached to the holder, and further comprises a tab, configured to align with the groove on the holder, to aid in holding the medical tool in the holder. In other embodiments, the door may be removable and/or replaceable.

One or more further embodiments of the subject disclosure include a method of guiding a medical instrument, comprising, mounting a medical guidance apparatus about a predetermined insertion point of a surface, the medical guidance apparatus comprising a base assembly including a base ring having an inner circumference defining an opening and a guide rotatably mateable with the base assembly, the guide including a frame having an inner circumference defining an opening and an outer circumference, wherein, in a configuration where the guide is mated with the base assembly, the opening of the frame overlays the opening of the base ring. The apparatus may further include an arc member and a holder slideably attached to the arc member, wherein the holder is configured to hold a medical tool intended to be guided by the medical guidance apparatus. The method may further include positioning the guide to a predetermined position relative to the base ring, positioning the medical instrument to a predetermined position upon the holder, and inserting the medical instrument through the insertion point.

The present disclosure, via one or more embodiments, achieves fundamental needle or multi-needle, or probe or multi-probe, configurations desired for procedures, such as, but not limited to, ablations, biopsy, diagnosis, treatment, etc., without multiple interchangeable probe guides.

One or more other features discussed herein may reduce the risk of user error, and may improve registration accuracy during device-to-image registration and may improve or optimize use after registration.

One or more features of one or more embodiments of the present disclosure may be used for various types of devices, such as, but not limited to, an MRI, Ultrasound or other scan devices instead of a CT scanner. One or more embodiments may be able to apply any position detectors instead of an encoder. One or more embodiments may use a speaker, vibrator or other lighting devices instead of light emitting diodes (LEDs) to help guide, manipulate and/or register a device, probe and/or needle. While ablation procedures are discussed above as one or more examples of needle guidance and placement, one or more embodiments may apply biopsy needles or other medical procedure needles instead of ablation needles.

In accordance with one or more embodiments of the present disclosure, needle guidance planning and performance and/or visualization and registration apparatuses and systems, and methods and storage mediums may operate to characterize biological objects, such as, but not limited to, lesions, tumors, critical structures, etc.

In accordance with at least another aspect of the present disclosure, the ablation probe or needle placement/guidance and/or device-to-image registration using a mask technique(s) discussed herein may be employed to reduce the cost of at least one of manufacture and maintenance of ablation planning and performance devices, systems and storage mediums by reducing or minimizing a number of components therein to cut down cost.

According to other aspects of the present disclosure, one or more additional apparatuses, one or more systems, one or more methods, and one or more storage mediums using masking to perform registration technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION

One or more devices, systems, methods and storage mediums for performing guidance for needles or probes and/or for visualization and manipulation of result(s) from device-to-image registration are disclosed herein. In one or more embodiments, the configurations, methods, apparatuses, systems and/or storage mediums may be combined to further enhance the effectiveness in guiding the needles or probes, including using one or more methods for visualization and manipulation of results from device-to-image registration to improve or optimize placement of the needle(s) and/or probe(s). Several embodiments of the methods, which may be carried out by the one or more embodiments of an apparatus, system and computer-readable storage medium, of the present disclosure are described diagrammatically and visually in FIGS. 1A through 20.

Figures 1A, 1B:
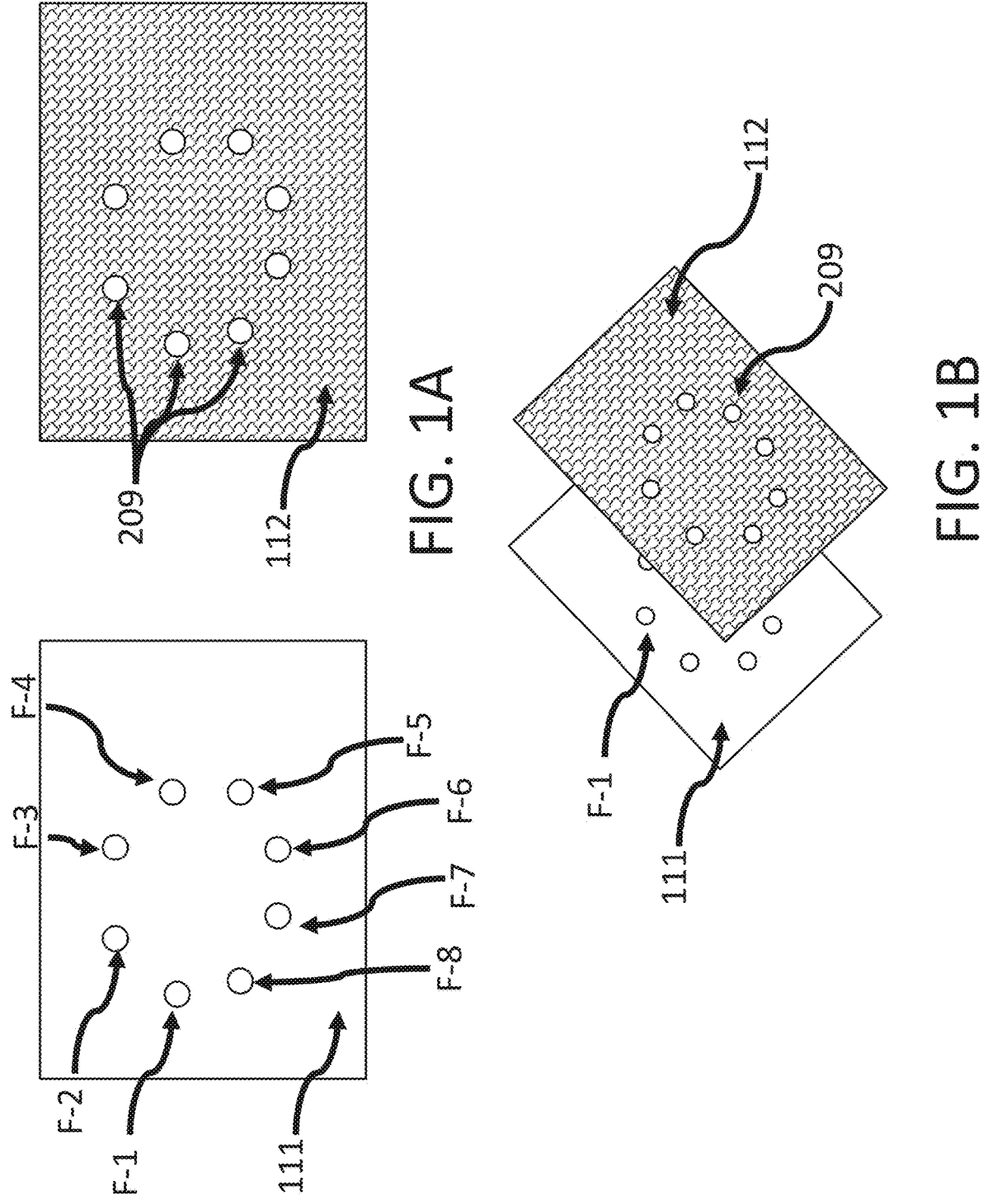
FIG. 1A is a schematic diagram showing at least one embodiment of a model fiducial plane and fiducials within an image in accordance with one or more aspects of the present disclosure.
FIG. 1B is a schematic diagram showing at least one embodiment of noise being introduced due to artifacts or noise in an image in accordance with one or more aspects of the present disclosure.

As shown in FIG. 1A, at least one embodiment of a model fiducial plane 111 are shown on the left side of the figure. For example, a model fiducial plane 111 may have one or more fiducials (e.g., F-1 through F-8) for use during registration. As shown on the right side of FIG. 1A, an image 112 may include one or more fiducials 209. In one or more embodiments, an environment is preferably provided where a model or device plane of known fiducial orientation (e.g., the plane 111) may be matched with an image (e.g., the image 112) including fiducials (e.g., the one or more fiducials 209). Preferably, the plane 111 and the image 112 are overlayed, and registration is performed.

As shown in FIG. 1B, in one or more situations, noise may be introduced due to artifacts or noise in an image (e.g., the image 112). For example, one or more artifacts or the noise may cause the model fiducial plane 111 and the image 112 to not be overlayed correctly, exactly or as planned.

Figure 2:
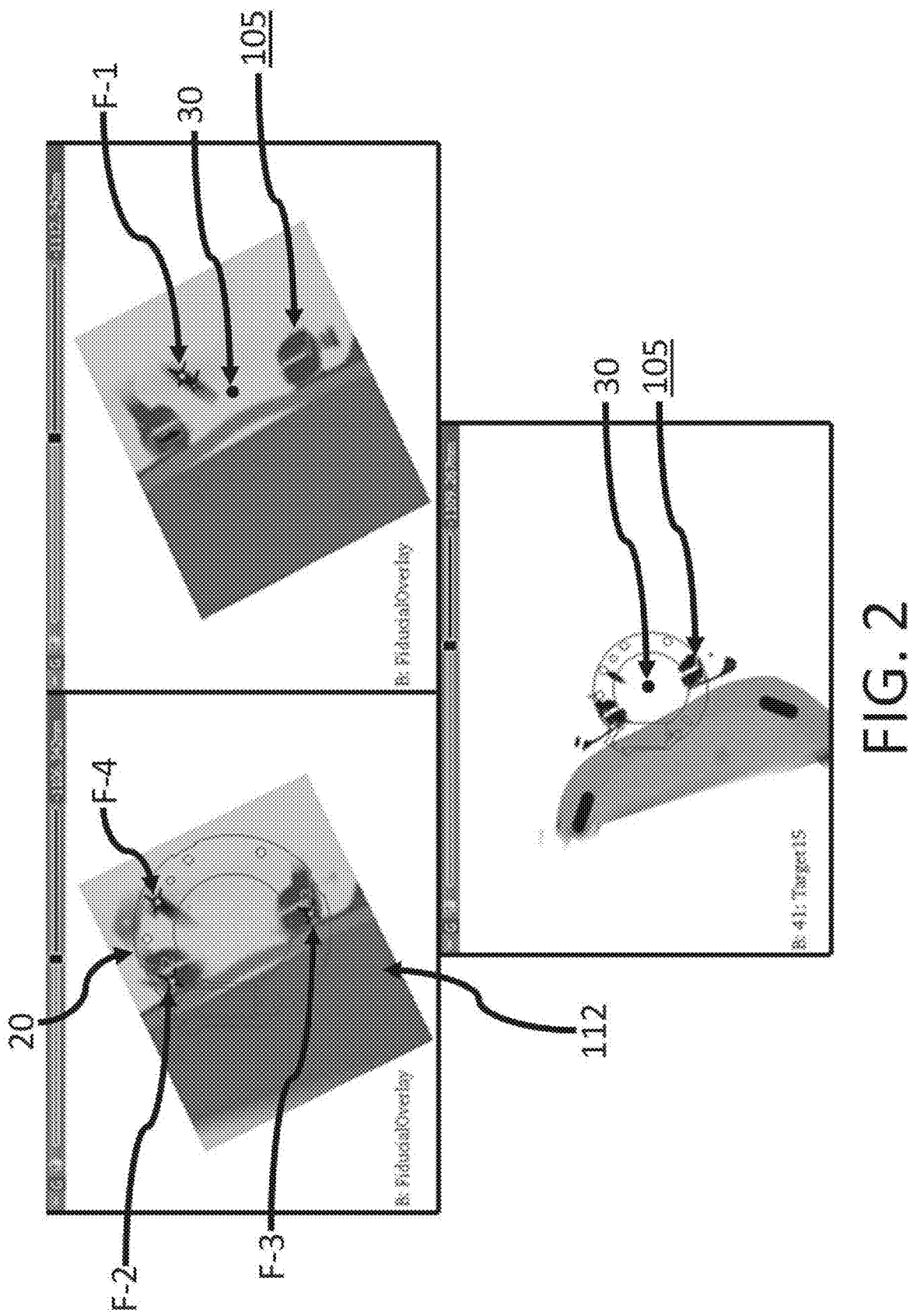
FIG. 2 illustrates a cropping window centered around a predetermined, specified insertion point to perform registration (e.g., automatic registration) with a fiducial model having a known fiducial orientation being overlayed on an image in accordance with one or more aspects of the present disclosure.

FIG. 2 illustrates a cropping window centered around a predetermined, specified insertion point 30 to perform registration (e.g., automatic registration) with a fiducial model (e.g., a model or plane 111 having fiducials F-1 through F-3, the plane 111, etc.) having a known fiducial orientation being overlayed on an image. FIG. 2 shows an instance in CT where a cropping window centered around the predetermined insertion point 30, in this case defined as a center of a patient mount unit (in other embodiments, the center point 30 may be determined before placement of a patient mount unit or a guidance device (see e.g., a guidance device 105 as shown in the bottom portion of FIG. 2 and as discussed below), may be determined as a predetermined location on a patient (e.g., without relation to a patient mount unit or a guidance device (see e.g., the guidance device 105 discussed below), is specified in order to perform automatic registration. An outline 20 represents the model with known fiducial orientation (e.g., the plane 111). The image 112 may include at least a patient mount unit or a guidance device (e.g., the guidance device 105 discussed below) with a needle placed on an imaging phantom used to assess the efficacy of registration performance. The patient mount unit (e.g., the guidance device 105 discussed below) preferably, in one or more embodiments, includes fiducials (e.g., the one or more fiducials 209) which may be used to be picked up by automatic preprocessing or processing algorithms in order for registration to take place. However, in at least one instance shown in the top two images of FIG. 2, a needle artifact may be mistaken for fiducials, greatly compromising the accuracy of registration. Since the needle (e.g., a needle 300 as discussed below, a biopsy needle, another needle for performing a medical procedure, etc.) is out of plane with respect to the axial orientation of CT slice acquisition, two different slices are shown at the top of FIG. 2 to indicate co-mingling of detection of actual fiducials (F-2 and F-3) with incorrect detection (elements incorrectly as fiducials F-1 and F-4, which are mistaking the needle artifact as fiducials as aforementioned). As such, one or more embodiments of the present disclosure may provide improved error detection using the subject approach or approaches.

Figure 3:
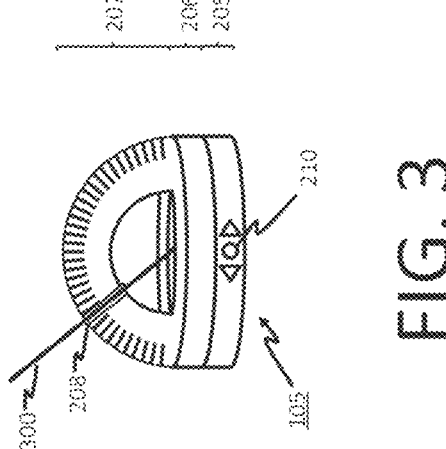
FIG. 3 is a schematic diagram showing an embodiment of a guidance device and/or system for performing needle guidance in accordance with one or more aspects of the present disclosure.
Figure 4A:
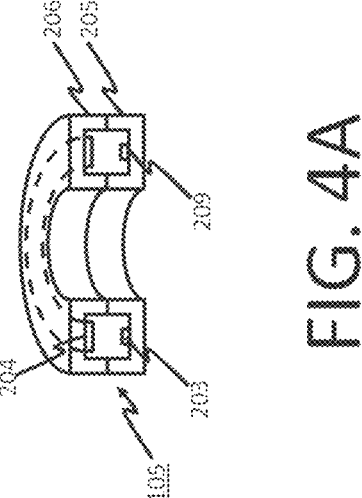
FIG. 4A is a schematic diagram showing a section view of the guidance device and/or system of FIG. 1 in accordance with one or more aspects of the present disclosure.
Figure 4B:
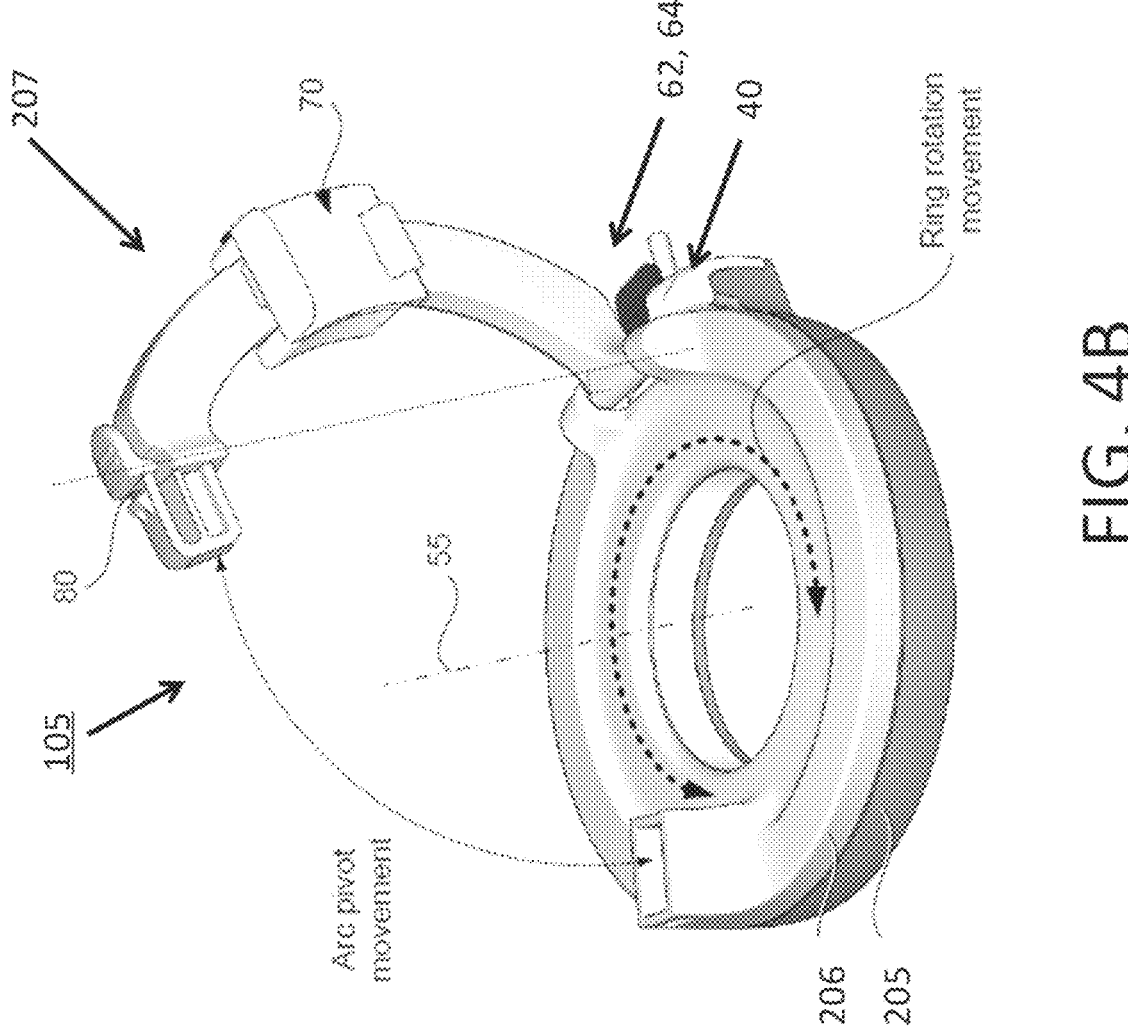
FIG. 4B is a schematic diagram showing an alternative embodiment of a guidance device and/or system in accordance with one or more aspects of the present disclosure.

In accordance with at least one aspect of the present disclosure, at least one embodiment of a device for guiding needles or probes, and for performing masking during device-to-image registration, may include structure from one or more embodiments as shown in FIGS. 3-4B. In FIG. 3 there is a guidance device 105, which preferably includes a fixed part 205 and a movable part 206. The guidance device 105 may include a processor 1201, 1201' (while reference number 1201' is used to indicate a "second" processor, the structure discussed herein and shown in the accompany figures for the processor or CPU 1201 may be used in one or more embodiments of the guidance device 105), a wireless or wired communication circuit 1205, 1212 (while reference numbers 1205 and 1212 refer to a communication interface and a network interface, respectively, as discussed below, the structure for both elements 1205 and 1212 may be used for the wireless or wired circuit in one or more embodiments of the guidance device 105), and an encoder sensor 203. The guidance device 105 may further include, or be used with, one or more fiducial markers 209, one or more light emitting diodes (LEDs) 210, and/or one or more batteries in one or more embodiments. A plurality of fiducial markers 209 may be included (embedded) in the device 105 (e.g., in the fixed part 205, in the movable part 206, etc.) for device to image (or device-to-image) registration.

In one or more embodiments, the movable part 206 may include an encoder scale 204. The encoder scale 204 may be fixed on the movable part 206. In one or more embodiments, the fixed part 205 and the movable part 206 are removably attached to each other such that the encoder sensor 203 faces or is disposed towards the encoder scale 204 in a case where the fixed part 205 and the moveable part 206 are attached as best seen in FIG. 4A. Alternatively, in one or more embodiments, the encoder scale 204 may be fixed on the fixed part 205, and the encoder sensor 203 may be disposed on the movable part 206 to achieve positional sensing between the fixed part 205 and the moveable part 206.

In one or more embodiments, the encoder sensor 203 operates to detect a relative position with respect to (and/or based on interaction with or sensing) the encoder scale 204. In embodiments where the encoder sensor 203 is fixed on the fixed part 205, relative displacement between the fixed part 205 and the movable part 206 may be detected by the encoder sensor 203 and/or an encoder.

Preferably, in one or more embodiments, the movable part 206 further includes an arc 207 as best seen in FIG. 3. A needle holder 208 is preferably attached on, or may be used with, the arc 207. Preferably, the needle holder 208 is movable along the arc 207, and the needle holder 208 operates to hold a needle by one or more methods, including, but not limited to, friction, pressure fitting, a clasp or grasping mechanism, etc. Preferably the arc 207 includes a scale (e.g., a tool for measuring an angle of the needle or other item being held by the holder 208) so that a user of the device or system 105 may read an angle at which the needle or other item being held by the holder 208 is oriented. In one or more embodiments, the arc 207 may be releasably connected to the movable part 206 such that the arc 207 may be released from the movable part 206 as needed. In one or more embodiments, the arc 207 may be integral with the movable part 206.

Preferably, in one or more embodiments of the device or system 105, fiducial markers 209 (see e.g., the fiducial marker 209 shown in FIG. 4A; see also, one or more of F-1 through F-8 in FIGS. 1A-2; etc.) may be used for registration of the device or system 105. Because fiducial markers 209 are visible in CT images, a processor, such as a first processor 1201 of a computer 2, 2' (see e.g., FIG. 13 as discussed further below, and FIGS. 19-20 as discussed further below, etc.) and/or the second processor 1201, 1201' of the guidance device or system 105, may calculate an orientation of the guidance device 105 based on the positions of a plurality of the fiducial markers 209, F-1 through F-8 (e.g., in a model plane (e.g., the plane 111) overlayed with an image (e.g., the image 112)), etc. In one or more embodiments, fiducial markers 209, F-1 through F-8, etc. may be implanted in the fixed part 205 and placed uniquely in a three dimensional (3D) space. Other types of fiducial markers may be used in one or more embodiments of the present disclosure. For example, fiducial markers (and methods, apparatuses and systems related to same) discussed in U.S. patent application Ser. No. 15/727,978, filed Oct. 9, 2017, the entirety of which is incorporated by reference herein, and as discussed in U.S. Pat. Pub. No. 2019/0105109, published on Apr. 11, 2019, the entirety of which is incorporated by reference herein, may be used in one or more embodiments.

An insertion angle of a needle 300 (e.g., one or more needles use for a medical procedure as discussed herein, such as, but not limited to, ablation, biopsy, etc.) is preferably guided by a combination of the scale on the arc 207, a position of the encoder sensor 203 and orientation of the guidance device or system 105 in one or more embodiments. If a user places the guidance device or system 105 on a designated or predetermined or predefined position, then the fiducial markers 209 may be optional or may not be used as needed. In such a step, a processor, such as the first processor 1201 of a computer 2, 2', the second processor 1201, 1201' of the guidance device 105, etc., does not need to calculate orientation in view of the preset orientation. That said, as further discussed below, preferably one or more embodiments of methods for visualization and manipulation of device-to-image registration use fiducials.

In one or more additional embodiments, the guidance device or system 105 may include additional or alternative features as discussed in U.S. Provisional Patent Application No. 62/764,849, filed on Aug. 15, 2018, the entirety of which is incorporated by reference herein, may include additional or alternative features as discussed in U.S. Provisional Patent App. No. 62/764,820, filed Aug. 15, 2018, the entirety of which is incorporated by reference herein, may include additional or alternative features as discussed in U.S. Provisional Patent App. No. 62/875,243, filed Jul. 17, 2019, the entirety of which is incorporated by reference herein, and may include additional or alternative features as discussed in U.S. patent application Ser. No. 16/539,769, filed Aug. 13, 2019, the entirety of which is incorporated by reference herein. For example, FIG. 4B illustrates a perspective view another embodiment of a medical guidance device or apparatus 105 having a guide or upper movable portion 206, a fixed portion 205, and an arc 207 using a hinge assembly 62, 64 (e.g., the arc 207 may be terminated at one end thereof with a hinge, such as, but not limited to, a c-shaped clip 62 to be disposed on, around or over a pin 64) where the hinge assembly 62, 64 is, for example, in an opened position or state. The fixed portion 205 and the moveable portion 206 are similar to a base assembly (e.g., the base assembly 2110) and a guide or upper movable portion (e.g., the guide or upper movable portion 2150), or the other base assembly 110 and the upper movable portion 150 of a guidance device or apparatus as discussed in U.S. Provisional Patent Application No. 62/764,849, as discussed in U.S. Provisional Patent Application No. 62/875,243, as discussed in U.S. Provisional Patent App. No. 62/764,820, and/or as discussed in U.S. patent application Ser. No. 16/539,769, the entireties of which applications are incorporated by reference herein (similar reference numbers represent corresponding features). In this configuration (best seen in FIG. 4B), the other end of the arc 207 has been un-clipped from the rotating ring of the moveable portion 206 and the entire arc 207, including the probe holder 70 (which is similar to other probe or needle holders, such as those discussed in U.S. Provisional Patent Application No. 62/764,849, discussed in U.S. Provisional Patent Application No. 62/875,243, discussed in U.S. Provisional Patent App. No. 62/764,820, and/or discussed in U.S. patent application Ser. No. 16/539,769), is removed out of an insertion path 55. In the open position, the arc 207 may be positioned in one or more orientations, for example, substantially perpendicular to a plane of the ring of the moveable portion 206 or the fixed portion 205. However, if more space is needed for access to the area of interest, the first end of the arc 207 may also be detached at the pivotable hinge assembly 62, 64. To that end, the pivotable hinge assembly 62, 64 may be designed in other ways known to those skilled in the art such that the hinge assembly 62, 64 operates to pivot as a hinge, and is not limited to the c-shaped clip 62 and pin 64 configuration. This design allows the guide device (guidance system) 105 to be used in a variety of interventional and/or medical procedures.

For example, during a needle insertion procedure, it is highly advantageous that the arc 207 is rigidly attached at both ends thereof to the ring moveable portion 206 (e.g., as shown in at least FIG. 3). However, either before or after needle insertion procedure, the arc 207 may be entirely separated (removed) from the ring of the moveable portion 206. As mentioned above, the fixed portion 205 is configured to be strapped onto the patient's body to avoid accidental movement. Therefore, at the beginning of a procedure, only the fixed portion 205 and the ring of the moveable portion 206 may be attached to the patient's body to give the physician the opportunity to arrange the guide device 105 on the precise location of needle insertion.

On the other hand, after a needle insertion procedure is completed, e.g., after a first needle has been inserted, the physician may need to access the insertion point for inspection or confirmation. In that case, the arc 207 may be unlocked from the ring of the moveable portion 206 by operating the snap joint locking mechanism 80, and then the arc 207 is pivotably rotated to the position shown in FIG. 4B. This gives access to the physician for the necessary observation and confirmation of needle insertion. In addition, if more room is necessary for access to the insertion area of interest, the arc 207 may be disengaged from the pin 64 (e.g., the c-shaped clip 62 may be disengaged from the pin 64) of the ring of the moveable portion 206 so that the entire arc 207 and the needle holder 70 may be removed from the ring of the moveable portion 206 and/or the moveable portion 206. However, even after the arc 207 and needle holder 70 are removed, the fixed portion 205 and the ring of the moveable portion 206 and/or the moveable portion 206 may still remain rigidly attached to the patient's body. To that end, a latch cam 40 may be provided at any position along the circumference of the ring of the moveable portion 206 to maintain the ring of the moveable portion 206 and/or the moveable portion 206 in a fixed (anti-rotating) position.

Therefore, in the event that a new needle-insertion procedure is being performed on the patient, e.g., in the case of having to use multiple needle-like instruments, the arc 207 including the needle holder 70 may be simply mounted back onto the ring of the moveable portion 206 and/or to the moveable portion 206 by engaging the pivotable hinge assembly 62, 64 (e.g., by reconnected the hinge clasp 62 to the pin 64) and click-mounting the arc locking mechanism 80. In this manner, this pivotable and removable arc 207 and the needle holder 70 may provide at least: (i) ease of access to the area of interest, (ii) stiff and rigid support for needle-like instrument insertion, (iii) precise guidance during instrument insertion, and (iv) effective repeatability of insertion because the fixed portion 205 and the ring of the moveable portion 206 and/or the moveable portion may remain rigidly attached to the patient's body at all times during a medical procedure.

One or more embodiments provide useful hardware for physically guiding planned needles along planned trajectories, and/or for using one or more masks to perform, or prior to performing, a device to image registration algorithm. Indeed, prior to performance of one or more medical procedures, it is useful to accurately position the guidance device 105, and one or more embodiments discussed herein allow a user of the guidance device 105 to apply one or more masks to suppress one or more objects (e.g., artifact(s), needle(s), metal, etc.), or to enhance one or more target region(s) of interest, to improve or optimize the accuracy of registration (e.g., automatic or manual registration) and to manipulate application(s) of such masks as discussed below.

Figure 5B:
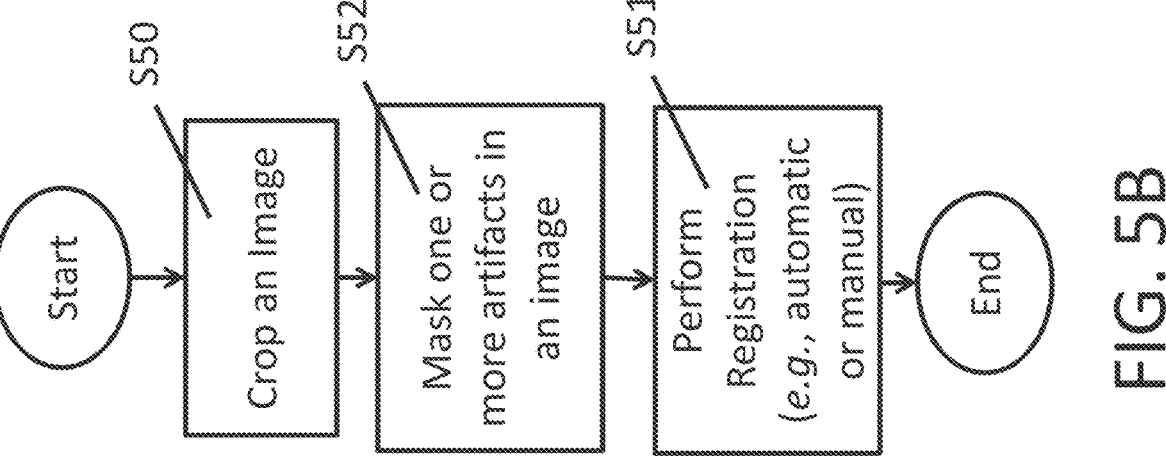
FIGS. 5A-5B are flow charts of at least one or more embodiments of a method of performing registration and a method of performing registration, including masking an artifact, respectively, in accordance with one or more aspects of the present disclosure.
Figure 5A:
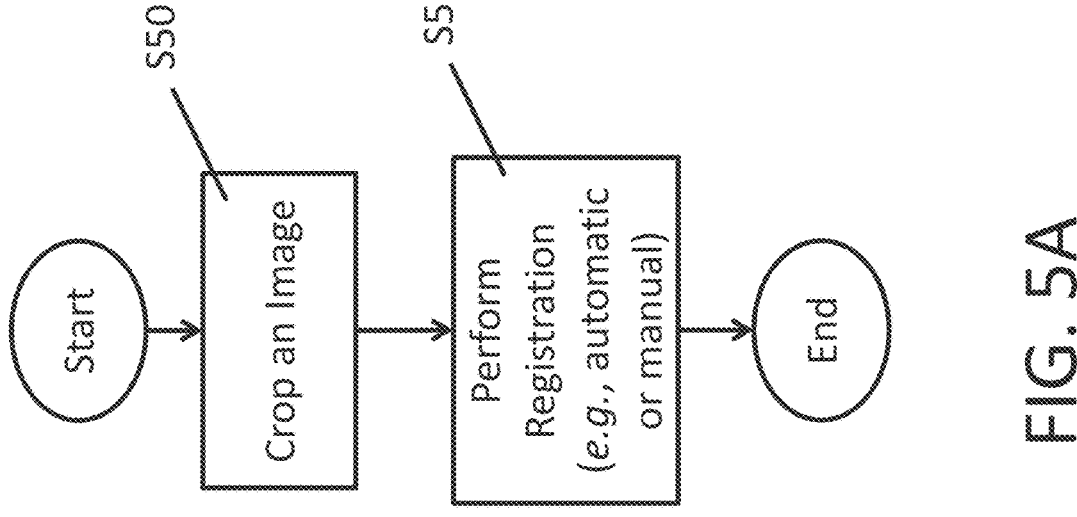

In one or more embodiments of methods for performing registration, the method(s) may include one or steps, including, but not limited to, one or more of the following: (i) cropping an image (see e.g., the cropped image 112 as shown in FIG. 2, etc.) (see step S50 in FIGS. 5A-5B); and (ii) performing registration (e.g., automatic or manual) (see step S51 in FIGS. 5A-5B). Preferably, in one or more embodiments, the registration processing and/or the registration pre-processing (e.g., processing occurring prior to registration) further includes masking one or more objects (e.g., one or more artifacts, one or more needles, one or more metal objects in a bed or support structure for a patient, etc.) (see step S52 as shown in FIG. 5B).

In one or more embodiments, masking may be approached as an automatic component of at least one pre-processing algorithm or a pre-processing pipeline for registration by incorporating known data. Using the aforementioned example from FIG. 2 for reference, the needle artifact may be masked utilizing the pre-planned insertion and target points.

Figures 6, 7:
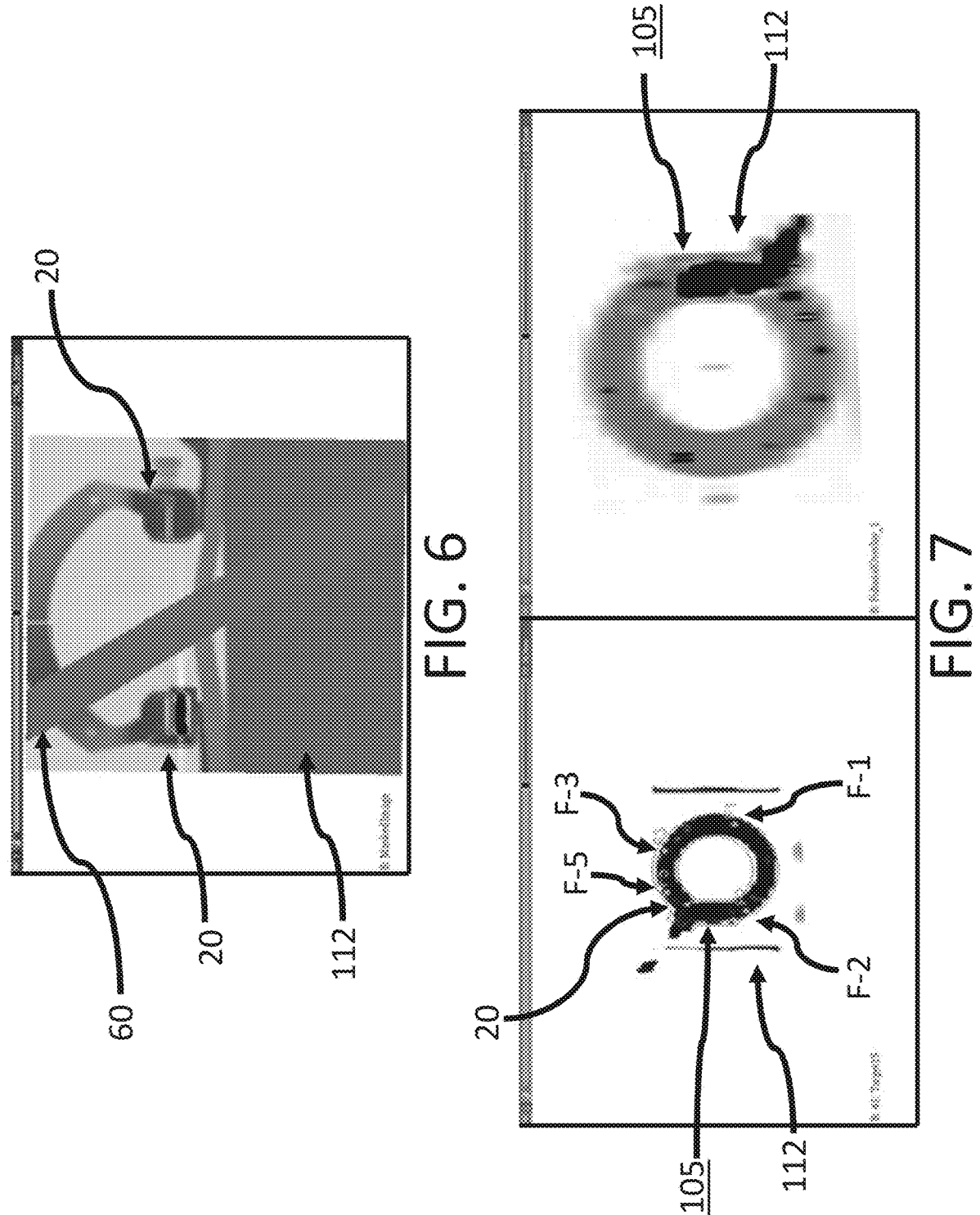
FIG. 6 illustrates at least one embodiment of a cropping window centered around a predetermined, specified insertion point to perform registration (e.g., automatic registration) including a fiducial model overlayed on the image after masking is performed in accordance with one or more aspects of the present disclosure.
FIG. 7 illustrates a cropping window centered around a predetermined, specified insertion point to perform registration (e.g., automatic registration) with a fiducial model having a known fiducial orientation being overlayed on an image where the fiducial overlay is using masking in accordance with one or more aspects of the present disclosure.

As best seen in FIG. 6, in one or more embodiments, masking of the needle artifact may be performed after cropping. However, in one or more embodiments, masking may occur prior to cropping, or may occur without performing the cropping step (e.g., a method embodiment may include steps S51 and S52 shown in FIG. 5B, but may not use step S50). Preferably, one or more embodiments use cropping and masking in concert to improve quality of the image or images. However, in one or more embodiments, cropping may be used alone, and/or masking may be used alone as aforementioned. In other words, the cropping and masking steps may be performed independently as needed in one or more embodiments. For example, in at least one embodiment the image 112 may be masked with at least one mask 60. In the subject example, the at least one mask 60 is placed over a needle (e.g., the needle 300) or any desired needle artifact. The masked image 112 may include the outline 20 of the fiducial model or plane in one or more embodiments. In one or more embodiments, the outline 20 may be shown in color (e.g., yellow, red, etc.) to allow a user to more easily view the outline 20. After masking is performed and the at least one mask 60 is added, registration (e.g., manual or automatic) is preferably performed.

Preferably, the device (e.g., the guidance device 105) has all fiducials 209, F-1 through F-8, etc. physically located in a single plane of the device 105 so that the physical plane may be matched with the model or plane 111 for registration. Obtaining the medical device may include, for example placing or securing the device 105 onto the patient over a surgical site. Medical image data may be obtained of the device 105 on the patient. The image data may be, for example, MRI or CT data.

The fiducial marker (e.g., fiducial markers 209, fiducials F-1 through F-8, etc.) objects from the medical image data, and/or the fiducial model or plane data, may be detected by an automatic registration algorithm in one or more embodiments.

In one or more embodiments, the model or plane 111 may be a virtual CAD model such that the detected fiducial locations may be matched to a virtual CAD model of the device 105 with known fiducial locations, and registration error may be calculated. The registration error value may be calculated as the mean square distance of the closest points between the detected fiducial markers (e.g., fiducial markers 209, fiducials F-1 through F-8, etc.) in the images and the template matched virtual model fiducial locations. In one or more embodiments, algorithm detected fiducial locations may be overlaid on some or all reconstructed images. Fiducial locations may, for example, be indicated by an overlaid dot on the images. In one or more embodiments, the calculated registration error allows for quick and intuitive visualization of the automatic device-to-image registration algorithm results.

In one or more embodiments, the user then decides whether registration is optimized or not. If there are clear mismatches between image locations of fiducials and the matched virtual model made visually apparent by the overlayed image and plane, then the user may adjust the mask, which may, in one or more embodiments, trigger a recalculation of the template match of the virtual fiducial device model and detected fiducial locations. Visually the user may quickly and easily match the virtual device model to the high intensity fiducials (e.g., F-1 through F-8, F-1, F-2, F-3, F-4, F-7, F-8, fiducial markers 209, etc.) in the images. The process continues until the user is satisfied with the registration results, and, once the user is satisfied, the user completes the registration process.

As best shown in FIG. 7, the fiducial overlay from FIG. 2 may be updated to include masking as aforementioned. The results show more accurate registration between the model 111 and the image 112. As shown in FIG. 7, the needle artifact(s) are not visible due to use of the at least one mask 60. Due to the use of the at least one mask 60, the fiducials shown (e.g., F-1, F-2, F-3, F-5, etc.) accurately represent the fiducial markers 209 included in the guidance device 105. Visually, the user may now confirm that registration is accurately or optimally performed, and may complete the registration process.

Figure 13:
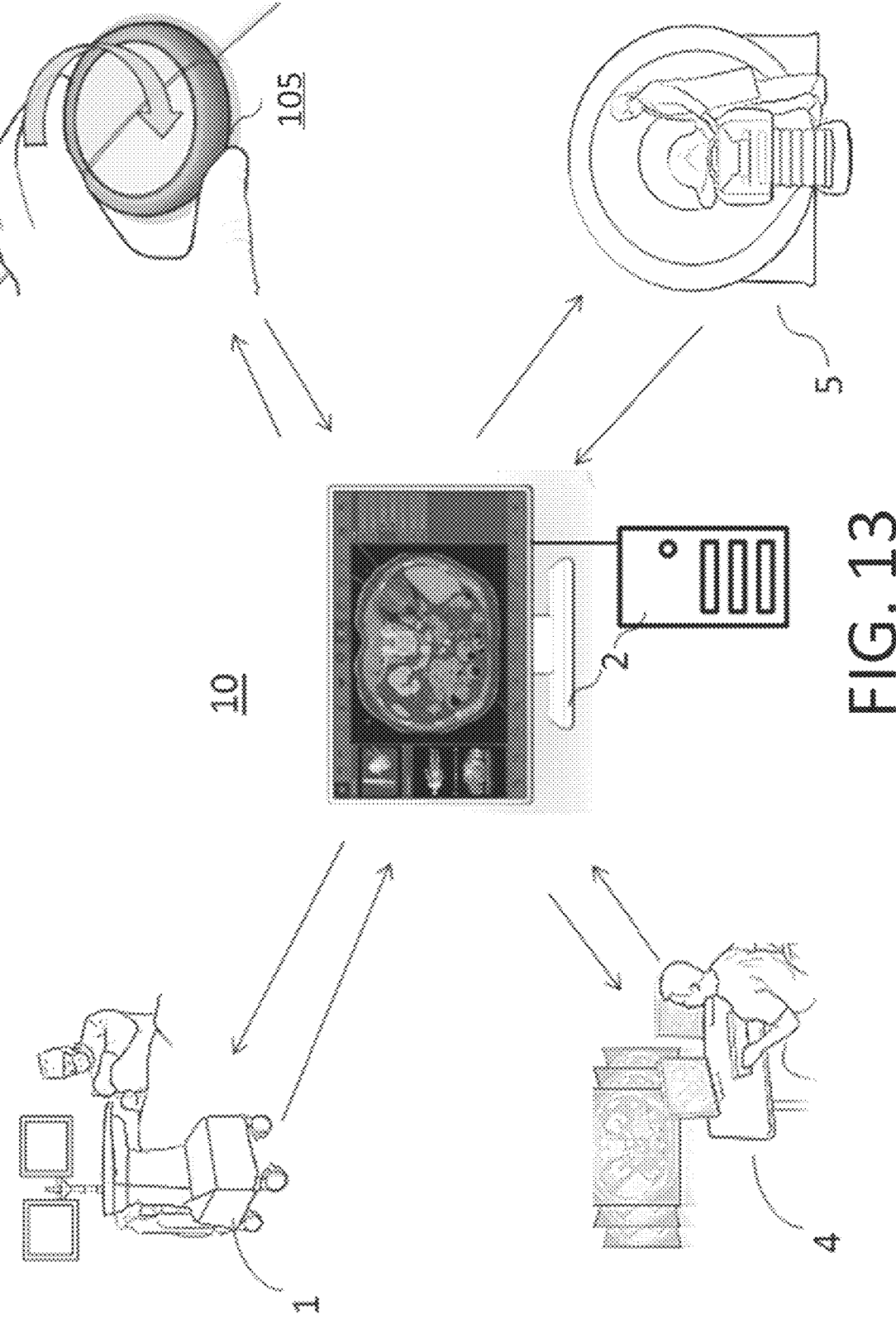
FIG. 13 is a schematic diagram showing an embodiment of a system for performing ablation and/or needle guidance planning and/or performance, and/or for performing registration using masking, in accordance with one or more aspects of the present disclosure.

In one or more embodiments of methods for performing registration with masking an artifact(s), the method(s) may include one or steps, including, but not limited to, one or more of the following: (i) acquiring image data (e.g., from a medical device 1 as shown in FIG. 13, a guidance device 105 as shown in FIGS. 3-4B and 13, from a scanner (e.g., the CT 5 as shown in FIG. 13), a PACS (e.g., the PACS 4 shown in FIG. 13) or other scanning device/system, or using a fresh or newly scanned image) (see step S800 in FIG. 8); (ii) selecting target and skin insertion point(s) (e.g., the insertion point 30 as shown in FIGS. 1B and 2, etc.) to plan needle insertion (see step S801 in FIG. 8); (iii) use the target and insertion point(s) (e.g., the insertion point 30 as shown in FIGS. 1B and 2, etc.) to create a proposed needle line trajectory (see e.g., insertion path 55 as shown in FIG. 4B, the direction of the needle in FIG. 3, etc.) (see step S802 in FIG. 8); (iv) translating the trajectory (see e.g., insertion path 55 as shown in FIG. 4B, the direction of the needle in FIG. 3, etc.) from pixel to patient space (see step S803 in FIG. 8); (v) identifying points a set or predetermined parameterized distance from the line or trajectory (e.g., to apply a mask, to apply a cylindrical mask, to apply a mask of a predetermined geometric size and shape, etc.) (see e.g., insertion path 55 as shown in FIG. 4B, the direction of the needle in FIG. 3, etc.) (see step S804 in FIG. 8); (vi) translating data back from patient to pixel space and assigning identified points a pixel value of a predetermined value (e.g., a value of 1, a value of −1000 for background air for example, a value based on the particular application(s) being achieved or intended during a procedure (e.g., the value may differ from one procedure to another or from one application to another), etc.) (see step S805 in FIG. 8); (vii) placing and imaging a device (e.g., the guidance device 105) (see step S806 in FIG. 8); and (viii) performing registration (e.g., automatic or manual) (see step S807 in FIG. 8).

Figure 9:
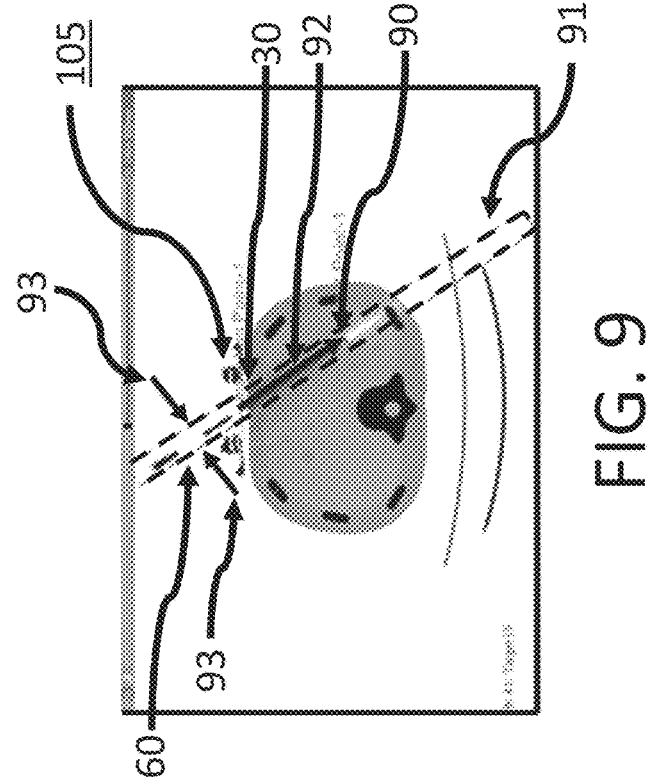
FIG. 9 illustrates a diagram for allowing a user to adjust a mask using one or more dimensions of a predetermined target, such as a needle, in accordance with one or more aspects of the present disclosure.

As shown in FIG. 6, a hard coded cylindrical area may be masked (see the at least one mask 60) around the trajectory (see e.g., insertion path 55 as shown in FIG. 4B, the direction of the needle in FIG. 3, etc.) defined by the planned insertion and target point (see e.g., the insertion point 30). In one or more embodiments, the target point may be different than the insertion point. For example, as shown in FIG. 9, the insertion point (e.g., the insertion point 30) may be located where a device, such as a needle, is inserted into a patient and the target point (e.g., the target point 90 as shown in FIG. 9) may be located where the medical procedure (e.g., biopsy, ablation, etc.) is to be performed. The cylindrical area of the at least one mask 60 may be indicated by a dashed line(s), box, or outline 91. In one or more embodiments, the user may set the insertion and target points 30, 90. In one or more embodiments, the at least one mask or masked area 60 may be user defined or more accurately fit based on user input, e.g., based on previously known needle dimension parameters, based on predetermined needle specifications, based on specifications of the guidance device 105, based on known details of the patient undergoing a procedure, based on the interactive image being viewed by the user (e.g., the user may click and drag the arrows 93 to adjust the thickness (or other arrows used for other dimensions (e.g., length, height, depth, etc.)) of the at least one mask 60, etc.

In a medical image, such as the CT image shown in FIG. 9, the arrow 92 indicates or represents a planned needle trajectory through the imaging phantom, where the dashed lines, box or outline 91 represent the proposed masking area. As aforementioned, the arrows 93 represent a user interaction, where the area of the at least one mask 60 may be adjusted. In one or more embodiments, the adjustment may be done automatically if the physical dimensions or specifications of the needle (or other medical device being inserted) are known or predetermined.

Figure 10:
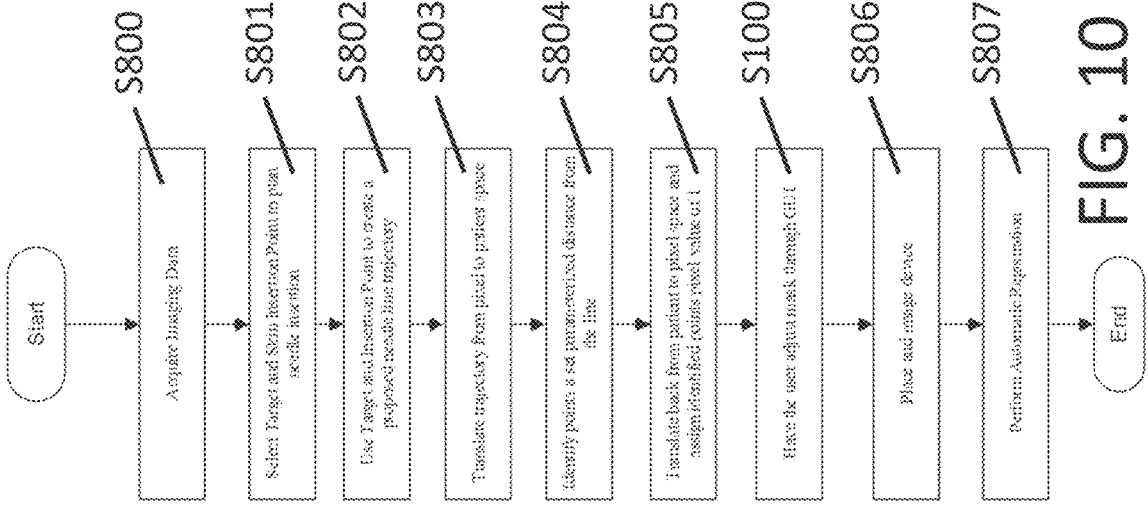
FIG. 10 is a flow chart showing at least one embodiment of a method for adjusting a mask for at least one predetermined target, such as a needle, in accordance with one or more aspects of the present disclosure.

Additionally or alternatively, in one or more embodiments the at least one mask 60 may be applied or modified/updated by user interaction (e.g., the user views an image and applies the at least one mask 60 using an input device (e.g., a keyboard (see e.g., the keyboard 1210 discussed below), a mouse (see e.g., the mouse 1211 discussed below), etc.). Such adjustment(s) or modification(s) may be inserted into the procedure shown in FIG. 8 as illustrated in FIG. 10 in one or more embodiments. The method for using a mask for performing registration as shown in FIG. 10 is the same as the method embodiment shown in FIG. 8 (such that the like-numbered method steps are discussed above, incorporated herein by reference and will not be repeated as a result), with the following exception: As shown in step S1000 in FIG. 10, a user may adjust the at least one mask 60 using a Graphical User Interface (GUI) (e.g., displayed on a screen such as the display 1209 discussed below). Step S1000 may be, for example, performed after step S805 and before step S806 as shown in FIG. 10. However, in one or more embodiments, steps may be moved around or performed in a different order, including, but not limited to, step S1000. In one or more embodiments, masking may be used for one or more reasons in addition to or other than (or instead of) registration. For example, masking may be used to make an object, an artifact or other target located in a background of an image or images less obscure.

Figure 8:
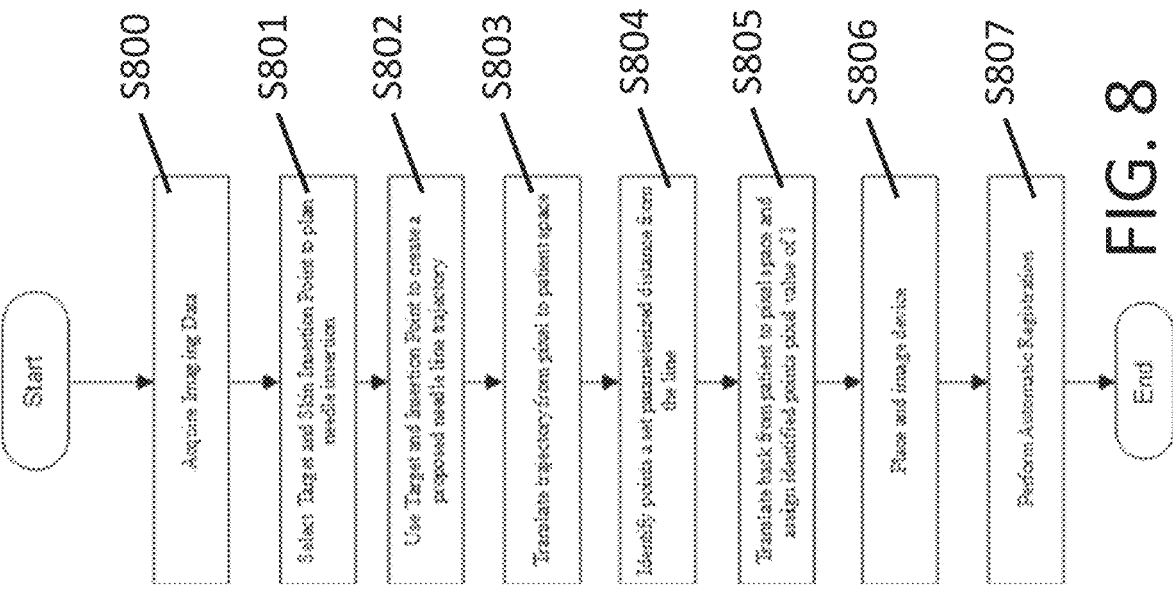
FIG. 8 is a flow chart showing at least one embodiment of a method for masking at least one artifact in accordance with one or more aspects of the present disclosure.
Figure 11:
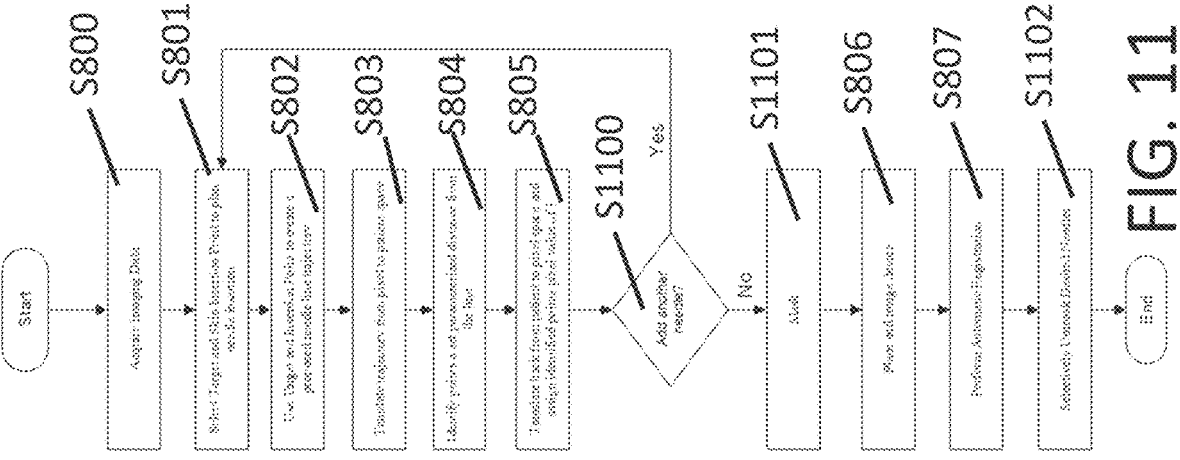
FIG. 11 is a flow chart showing at least one embodiment of a method for masking one or more needles except for a target or current needle in accordance with one or more aspects of the present disclosure.

Additionally or alternatively, one or more embodiments for performing a method for masking one or more needles or devices except for a target or predetermined needle or device may include the one or more of the steps shown in one or more of FIG. 8 and FIG. 10 and as discussed above. For example, as shown in FIG. 11, one or more embodiments of a masking method involving multiple needles (e.g., with different planned trajectories) may use the steps shown in FIG. 8 (such that the like-numbered method steps are discussed above, incorporated herein by reference and will not be repeated as a result), and may further include one or more of the following steps: (i) after step S805, a determination is made as to whether another needle (e.g., another ablation needle 300, another biopsy needle, etc.) is being added to the image or whether a planned trajectory for that needle is being added to the image (see step S1100 in FIG. 11). In a case where the determination results in a "Yes" answer, then the method returns to step S801 and repeats steps S801 through S805 for each additional needle or planned trajectory for that needle as shown in FIG. 11. In a case where the determination results in a "No" answer, then the method proceeds to adding, finalizing, applying or placing the mask(s) to the multiple devices or needles in the image (see step S1101). Then the method proceeds to steps S806-S807 as described above. Thereafter, a user may further selectively unmask desired needles (see step S1102) in one or more embodiments, for example, when the user wants to highlight such desired needles in the image before, during or after a medical procedure. As such, masking may be used to highlight the current target needle or needle of interest. As aforementioned, in one or more embodiments, masking may be used for one or more reasons in addition to or other than (or instead of) registration. For example, masking may be used to make an object, an artifact or other target located in a background of an image or images less obscure.

Figure 12:
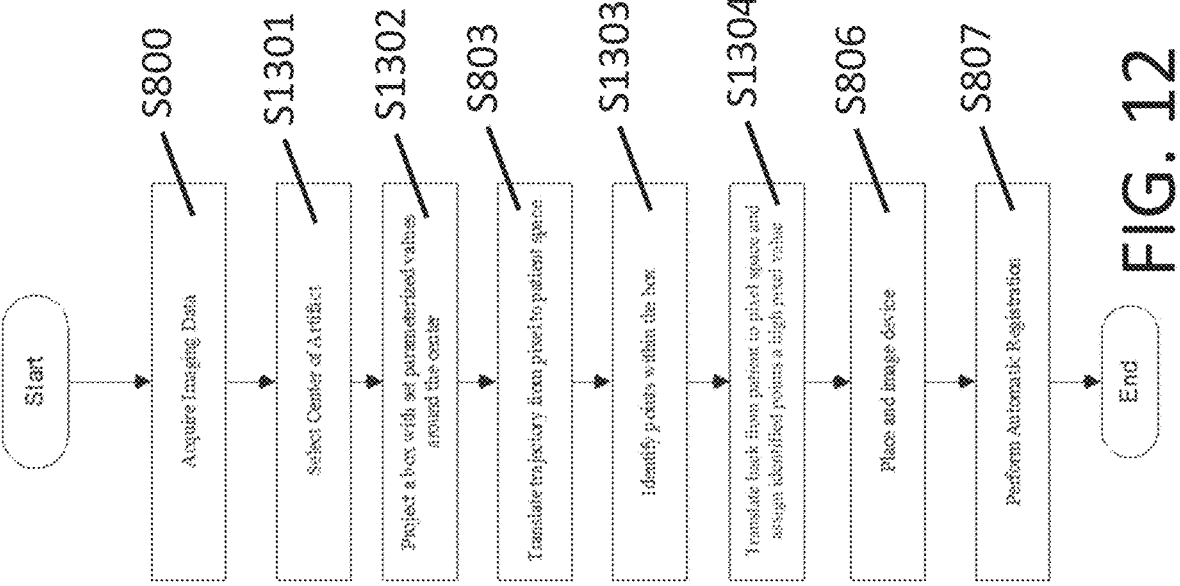
FIG. 12 is a flow chart showing at least one embodiment of a method for using a mask to enhance a region or regions of interest in accordance with one or more aspects of the present disclosure.

As aforementioned, masking may be used to enhance regions of interest, not just for suppression. This may be useful in cases where fiducials are obscured by noise. For example, one or more embodiments for performing masking to suppress one or more artifacts or objects in an image, may include steps S800, S803, S806, and S807 (discussed above such that the like-numbered method steps are incorporated herein by reference and will not be repeated) as shown in FIG. 12. One or more methods for suppression via masking may further include, but are not limited to, one or more of the following steps: (i) selecting a center or a predetermined location of an artifact to be suppressed (see step S1301 in FIG. 12) (e.g., after performing step S800); (ii) projecting a box (or other geometrically-shaped indicator, such as, but not limited to, a cylinder, a vessel shape, etc.) with set parameterized value(s) around the center or the predetermined location of the artifact (see step S1302 in FIG. 12); (iii) identifying points within the box (or other geometrically-shaped indicator, such as, but not limited to, a cylinder, a vessel shape, etc.) (see step S1303 in FIG. 12; e.g., which may be performed after step S803); and (iv) translating back from patient to pixel space and assigning identified points a high pixel value (see step S1304 in FIG. 12).

Structure of the guidance device 105 may incorporate one or more features as discussed in U.S. Provisional Patent Application No. 62/764,849, filed on Aug. 15, 2018, which is incorporated by reference herein in its entirety, and as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties. For example, the fixed portion 205 and the moveable portion 206 may operate using a bearing. The bearing may be a ball bearing or any other suitable bearing structure known in the art that allows for relative motion between two concentric rings or similarly sized and/or shaped mating portions of the device or system 105. For example, the bearing may be a plain bearing, a roller bearing, and the like. The fixed portion 205 may further include a seal, which protects the bearing by preventing contamination from the external environment from coming into contact with the bearing. In one or more embodiments, the fixed portion 205 may further include a grip. The grip may be attached to or integral with the fixed portion 205. The grip provides a mechanism for the operator to increase stability of the fixed portion 205 during insertion of the medical instrument. Additionally, the grip may house electronic components relating to the use of LED arrays, which are used to indicate information to the user. The grip may also include visible markers for the medical images. In one or more embodiments, the fixed portion 205 and/or the movable portion 206 may include a gap that operates as an interruption to permit a medical instrument to pass through the gap and into the opening of the guidance device 105. The medical instrument can be an ablation probe in cryoablation, microwave ablation, radiofrequency ablation, laser ablation and irreversible electroporation ablation. Also, the medical instrument can be a needle-like device, for example a biopsy needle, an aspiration needle and a drainage needle. The gap may include the width wide enough to get the medical instrument through for releasing/accepting.

The arc member 207 has an arc shape that spans an angle relative to the horizontal plane (see e.g., FIGS. 3 and 4B). The angle 170 may be from 60 to 170 degrees, more preferably 120 to 150 degrees. The angle may be from 0 to 180 degrees in one or more embodiments. The arc member 207, as aforementioned, may include a guide surface that provides a guidance area for the instrument. The arc member 207 may include a plurality of angular reference marks on the guide surface (as shown, for example, in FIG. 3). The surface of the arc member 207 may have a different color than the color of the surface on the opposite side of the arc member 207. Having a different color allows the operator to quickly and easily ascertain which surface is the guide surface. This is particularly useful in an embodiment which lacks the plurality of reference marks. The angular reference marks signify an angle around a center point of the opening of the guidance device 105.

The angular reference marks may be visible optically as well as in CT and X-ray images utilizing radio-opaque material. The radio-opaque material may be, but is not limited to, plastic including fillers of barium sulfate, bismuth subcarbonate, bismuth oxychloride, tungsten, etc. The arc member 207 may have a thickness. The thickness may be $1/15$ to $1/3$ the diameter of the opening of the guidance device 105, more preferably $1/12$ to $1/5$ the diameter of the opening, more preferably $1/10$ to $1/5$ the diameter of the opening. In various embodiments, the angular reference marks may be provided on the thickness portion of the arc member 207, thus allowing for viewing of the angle from a top perspective. The angular reference marks may be envisaged in any desired increment and/or scale, with various increments being sized differently for indication purposes.

The ends of the arc member 207 may be integrally formed with the frame of the moveable portion 206 such that the entire upper or first portion (e.g., the moveable portion 206 and the arc member 207) of the device 105 and/or the device 105 is monolithically formed. That is, the entire upper or first portion (e.g., the moveable portion 206 and the arc member 207) of the device and/or the device 105 may be cast as a single piece of material. Alternatively, as shown in FIG. 4B, the arc portion or member 207 may include the hinge assembly 62, 64 and the locking mechanism 80 as discussed above.

In some embodiments, the plurality of angular reference marks on the guide surface of the arc member 207 may comprise LED indicators. These LED indicators provide illumination of the guide surface or they may be turned on to indicate, for example, an angle of planned entry (e.g., a lit indicator appears at the planned entry angle). For a medical guidance apparatus that is configured to detect the angle of a needle positioned in or near the medical guidance apparatus, the LEDs may be used to display when the needle is approaching or at a 'correct angle' by, for example, signaling with a green light at that angle.

Each of the monolithic structure of the first or upper portion (e.g., the moveable portion 206 and the arc member 207), the device 105, etc. contributes to one or more structural advantages. For example, when force is applied to the arc member 207 in a direction against the guide surface of the arc member 207, one or more of these structural features provide sufficient stiffness and rigidity to provide support and to minimize deflection, thereby providing sufficient support to the user when position an instrument. This structure provides a high rigidity while the structure still provides an opening for needle egress. This is in contrast to a cantilever shape, i.e., an open frame. The monolithic structure has a greater stiffness and may withstand the forces associated with needle placement and maneuvering with smaller deflection.

Additionally, because of the monolithic structure(s), assembly error may be avoided in one or more embodiments. The structure of the guidance device 105 and/or the upper or first portion (e.g., the moveable portion 206 and the arc member 207) is able to provide this structural support despite having the aforementioned gap in one or more embodiments.

As noted above the upper or first portion (e.g., the moveable portion 206 and the arc member 207) of the guidance device 105 may be rotatably coupled with the fixed portion 205. In one aspect, this may be achieved by mechanically coupling the frame of the upper or first portion (e.g., the moveable portion 206 and the arc member 207) of the guidance device 105 to the moveable portion 206 via a mechanical interface as discussed in U.S. Provisional Patent Application No. 62/764,849, filed on Aug. 15, 2018, the entirety of which is incorporated by reference herein, and/or as discussed in U.S. Provisional Patent Application No. 62/764,849, as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties. The mechanical components may be any suitable mating structure such as corresponding male/female components, snap fitting, bayonet mount and Velcro-style fastener, and the like.

Once the upper or first portion (e.g., the moveable portion 206 and the arc member 207) of the guidance device 105 is mated with base assembly 110 via the moveable portion 206, the upper or first portion (e.g., the moveable portion 206 and the arc member 207) of the guidance device 105 is able to freely rotate via the moveable portion 206. That is, the moveable portion 206 being rotatable about an axis relative to the stationary fixed portion 205 (as described above), and the upper or first portion (e.g., the moveable portion 206 and the arc member 207) of the guidance device 105 being coupled with the moveable portion 206, allows the upper or first portion (e.g., the moveable portion 206 and the arc member 207) of the guidance device 105 and the moveable portion 206 to rotate together about the axis when a rotational force is applied to either the moveable portion 206 or the upper or first portion (e.g., the moveable portion 206 and the arc member 207, a part of the arc member 207, etc.) of the guidance device 105.

In one or more embodiments, the guide or moveable portion 206 may be attached to an arc member 207, as shown in FIG. 2B, comprising a rail and an instrument holder 70. The arc member 207 may define the rail along which the instrument holder 70 may slide. The instrument holder 70 may be in the shape of a half cylindrical groove sized to receive an instrument, for example a needle (see e.g., the needle 300). The instrument holder 70 may be shaped to fit other instruments, depending on the procedure being conducted. The instrument holder 70 may provide constrained guidance for the instrument, such as the needle (e.g., the needle 300). The instrument holder 70 may accurately guide the instrument, such as the needle (e.g., the needle 300), by directing the half cylindrical groove to the target trajectory. Thus, the instrument holder 70 may increase accuracy and may reduce intervention.

The instrument holder 70 may be shaped to fit multiple instruments in a pre-set geometric configuration, for example multiple cryo-ablation needles arranged so the two or more needles will be held by the instrument holder 70. For example, two needles may be held simultaneously, both positioned near the arc member 207 or tangential to the arc member 207. In other examples, three, four, or more needles may be held simultaneously by the instrument holder 70 in a triangle, square, diamond, etc. configuration. The instrument holder 70 may provide constrained guidance for the instruments to maintain the geometric relationship between instruments (e.g., parallel insertion) during the procedure.

Another optional feature of some embodiments is a differentiating marker located on the guide or the movable portion 206. The differentiating marker is shown as a different color or hue located on the surfaces of the guide or movable portion 206 visible during use. This differentiates the portion of the medical guidance apparatus, device or system where the needle will be placed and guided. The differentiating marker may be, for example, a different color, an adhesive, a pattern, or some other differentiator that the physician or clinician can use to quickly differentiate which portion of the device should be used during needle placement.

In accordance with at least one aspect of the present disclosure and as aforementioned, one or more methods for performing needle guidance planning and/or performance and one or more methods for performing registration using masking are provided herein. At least FIGS. 13-20 illustrate flow charts of at least one respective embodiment of a method for performing needle guidance and/or performance using a guidance device (e.g., such as a device 105 as shown in FIG. 13), system (e.g., such as a system 10 as shown in FIG. 13) or storage medium. At least one embodiment of a system 10 may include a medical device (e.g., an ablation device, a biopsy device, etc.) 1, a needle guidance planning and/or performance computing system (which may include software and/or hardware for implementing the needle guidance planning and/or performance) or computer/processor 2 (alternative embodiment of a computer 2' that may be used is discussed herein below), a guidance device (such as, but not limited to, an image-plane localizer) 105, a Picture Archiving and communication system (PACS) 4 and an image scanner 5 (such as, but not limited to, a CT scanner, MRI device or other scanning apparatus). As shown diagrammatically in FIG. 13, the needle guidance planning and/or performance methods and/or visualization and manipulation of registration result(s) methods of the present disclosure may be involved with all major aspects of guidance planning and performance, including guiding one or more needles or other medical devices. For example, the system 2 may communicate with the image scanner 5 to request information for use in the guidance planning and/or performance, such as, but not limited to, bed or slice positions, and the image scanner 5 may send the requested information along with the images to the system 2 once a clinician uses the image scanner 5 to obtain the information via scans of the patient. By way of another example, the system 2 may communicate (wirelessly or in a wired configuration) and be used with a guidance device (also referred to as a locator device) 105 (such as an image-plane localizer that may be a patient-mount device and may be rotated as shown to help locate to biological object, such as a lesion or tumor; the aforementioned embodiments shown in at least FIGS. 2-4B and as otherwise discussed above may also be employed in the system 2 as the guidance device) to obtain information from the patient when conducting needle guidance planning and/or performance. The system 2 may further communicate with a PACS 4 to send and receive images of a patient to facilitate and aid in the needle guidance planning and/or performance. Once the plan is formed, a clinician may use the system 2 along with a medical device (e.g., an ablation device, a biopsy device, etc.) 1 to consult a chart or plan (e.g., for needle guidance, for ablation, for biopsy, for a medical procedure, etc.) to understand the shape and/or size of the targeted biological object to undergo the medical procedure (e.g., ablation, biopsy, etc.). Each of the medical device 1, the system 2, the guidance device 105, the PACS 4 and the scanning device 5 may communicate in any way known to those skilled in the art, including, but not limited to, directly (via a communication network) or indirectly (via one or more of the other devices 1, 105 or 5; via one or more of the PACS 4 and the system 2; via clinician interaction; etc.). In one or more embodiments as discussed herein, the guidance device 105 may communicate wirelessly with one or more of the following: the medical device 1, the system 2, the PACS 4, and the scanning device 5. Preferably, in one or more embodiments, the guidance device 105 communicates wirelessly or in a wired connection with at least the system 2 or any other processor operating to interact with the guidance device 105 to perform the guidance planning and/or performance and/or the visualization and manipulation of registration result(s).

One or more embodiments of the guidance planning and performance and/or the visualization and manipulation of registration result(s) apparatuses and systems, and methods and storage mediums may operate to improve the determination of the needle or probe (and/or other medical device) trajectory. One or more embodiments of the present disclosure operate to reduce the number of scans, and consequently reduce the insertion and trajectory determination time. One or more embodiments greatly assist clinicians, including during the stages of determining insertion point, determining trajectory, performing initial probe insertion and performing full probe insertion, by providing a probe tracking and guidance system for faster execution of the medical procedure and needle guidance plan and better accuracy in positioning a probe or other medical device. The tracking and guidance system not only tracks the probe, needle, guidance device, and/or other medical device position and orientation, but also provides cues for visualization software with the target biological object (e.g., a patient's lesion, a patient's tumor, etc.) and critical structures from an IR's or other clinician's point of view. This visualization may be updated in real time to account for motion due to respiration and tissue deformation. The tracking and guidance system can also give IR the ability to define the trajectory and insert the probe remotely through a robotic device placed on the body of the patient or situated near the patient, controlling the probe from outside of the imaging (CT for example) suite. The remotely controlled operating system may shorten procedures by reducing the time moving in and out of the CT suite and mitigating the exposure to radiation.

In one or more embodiments, multi-probe or multi-needle guidance may be used in combination with any feature disclosed herein, including, but not limited to, guidance of the one or more needles or one or more probes (including wireless guidance thereof), with a margin map, with a medial axis or center line, with a security or credential check, etc. In one or more embodiments, the size and shape of a biological object, such as a lesion or tumor, may be used to determine whether two or more needles, and two or more probes/balloons, are needed to appropriately perform a medical procedure on the target area of the biological object (e.g., ablate a target ablation zone). In one or more embodiments, clinicians may employ a spherical balloon(s) for an ablation zone because it is easy to control. In one or more embodiments, the balloon or balloons may have a different shape, e.g., elliptical or other predetermined shape. Additionally or alternatively, the type of balloon and number of balloons/needles may vary depending on the type of ablation being performed. For example, when performing microwave ablation, RF ablation, laser ablation and/or cryoablation, a spherical balloon may be used or the ablation may require a shape other than spherical. Multi-probe or multi-needle procedures are useful. For example, ablation may be performed with two needles and multiple balloons to ablate a target ablation zone for a biological object, such as a tumor or lesion. The methods disclosed herein may be used to simulate or perform guidance planning when evaluating a biological object or a target/target zone and determining whether to use a two-needle (or more) insertion for a desired medical procedure (e.g., ablation, biopsy, etc.).

Preferably the image scanner 5 (best seen in FIGS. 13 and 14) (e.g., a CT scanner) operates to generate one or more images from scanning a patient body (or portion thereof) with and/or without the use of the guidance device 105.

At least a first processor (e.g., a processor or CPU 1201 of the system 2 shown in FIG. 13, the first processor 1201 of FIG. 14, a processor or CPU 1201 in a device as shown in system 2 of FIG. 19, a processor or CPU 1201 as shown in system 2 of FIG. 20, a processor or CPU 1201 in another device, etc.) operates to load scanned images (e.g., from the PACS 4 generally as aforementioned because scanned images may be stored in the PACS 4). In one or more embodiments, the first processor 1201 operates to load images from the image scanner 5 and/or from the PACS 4. The first processor 1201 preferably supports users (e.g., physicians, clinicians, etc.) to plan and/or perform needle or medical device guidance trajectories (which may include or involve one or more of insertion angle(s), depth(s), region(s) of target(s) or interest(s), ablation power and duration if users use ablation needles, etc.). In one or more embodiments, the first processor 1201 may register scanned images and the guidance device 105 to calculate parameter(s) of one or more trajectories, fiducial locations, etc. In one or more embodiments, the first processor may read position information from an encoder (e.g., the encoder sensor 203) through a wired or wireless connection.

The first processor 1201 may detect fiducial markers (e.g., the aforementioned fiducial markers 209, F-1 through F-8, any of F-1 through F-8, etc.) from images (e.g., CT images) automatically or may detect fiducial markers via manual user interaction. As aforementioned, detection of fiducial markers may not be needed when the guidance device 105 is placed on a designated or predefined position. In one or more embodiments, the first processor 1201 may operate to reconstruct oblique image(s) (although this is an optional feature that may not be used, for example, in a case where the system (e.g., the system 2) does not show reconstructed oblique images on a display (e.g., the display 1209 of FIG. 14, the display of FIG. 13, the display or screen 1209 of FIG. 19, etc.). The first processor 1201 may allow users to compare pre-procedure images and post-procedure images (e.g., images taken before and after ablation).

Figure 14:
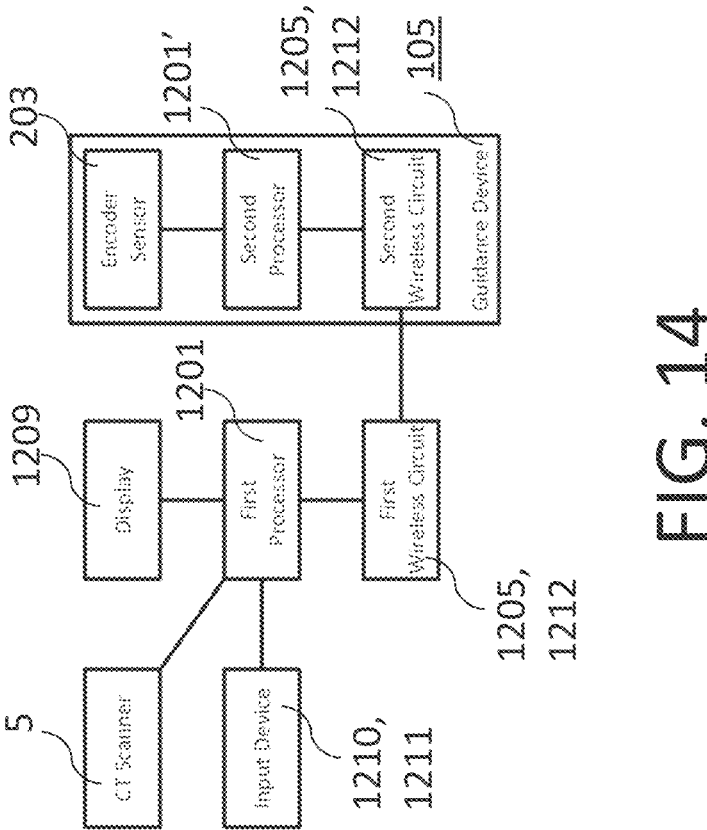
FIG. 14 is a schematic diagram of at least one embodiment of a communication signal and/or electrical connection(s) between a first processor and a second processor of a guidance device and/or system in accordance with one or more aspects of the present disclosure.
Figure 19:
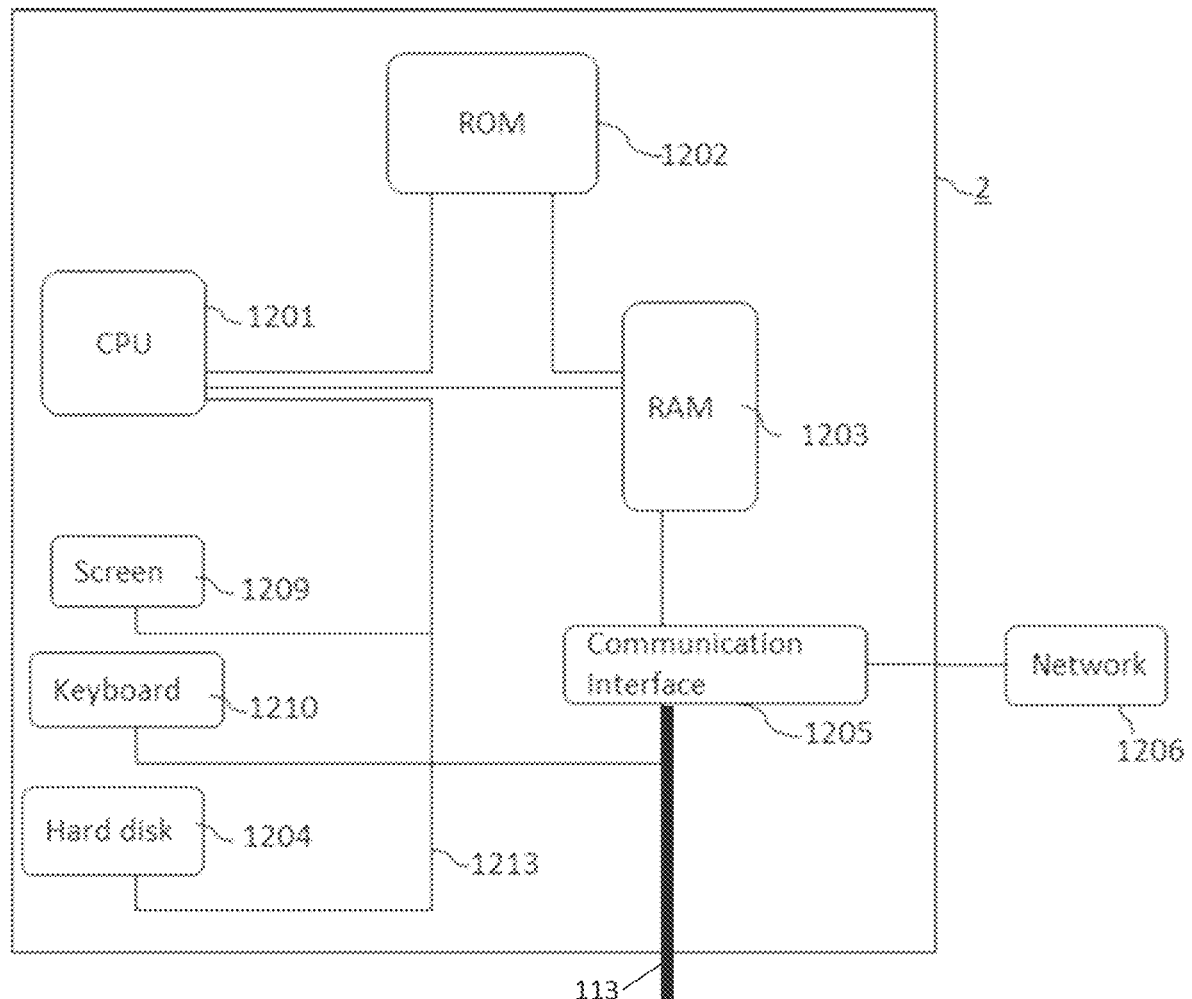
FIG. 19 shows a schematic diagram of an embodiment of a computer or processor that may be used with one or more embodiments of a needle guidance and/or performance method, apparatus or system in accordance with one or more aspects of the present disclosure.
Figure 20:
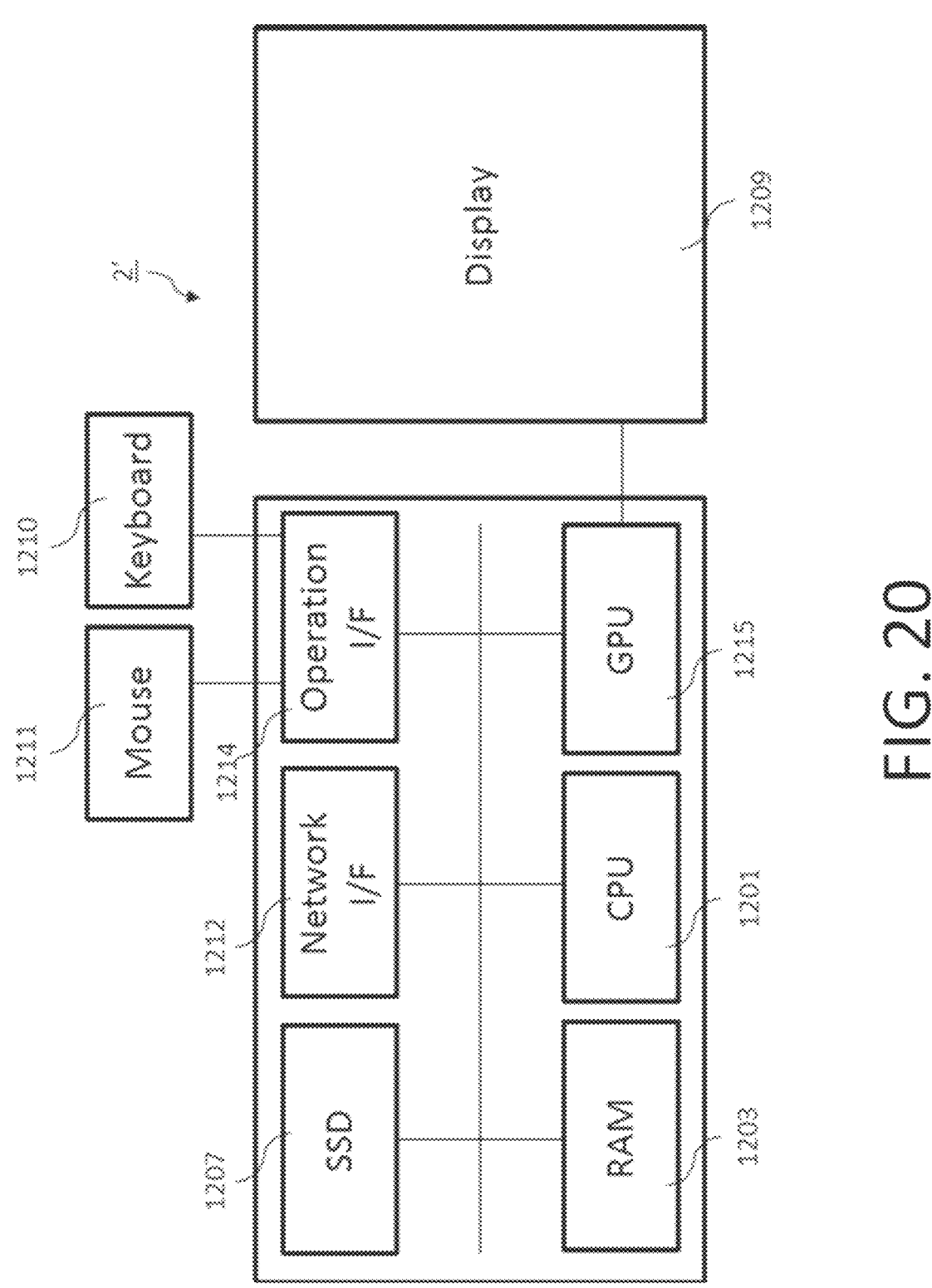
FIG. 20 shows a schematic diagram of another embodiment of a processor or computer that may be used with one or more embodiments of a needle guidance and/or performance method, apparatus or system in accordance with one or more aspects of the present disclosure.

A display (e.g., the display 1209 of FIG. 14, the display of FIG. 13, the display 1209 of FIG. 19, etc.) is preferably used in one or more embodiments to enable user interaction with an input device (e.g., a keyboard 1210 and/or a mouse 1211 as best seen in FIGS. 14 and 19-20). The display (e.g., the display 1209) may operate to do at least one or more of the following: show scanned images (e.g., CT images), show status (e.g., of the patient, procedure, one or more needles, etc.), visualize trajectories, compare pre-procedure and post-procedure images, etc.

Preferably, the first processor 1201 is connected to, and/or communicates with, a first wireless circuit (e.g., first wireless circuit 1205, 1212 as shown in FIG. 14, communication interface 1205 as shown in FIG. 19, network interface as shown in FIG. 20 (which may operate as a wired and/or wireless communication circuit), etc.) to enable communication between the first processor 1201 and at least a second processor (e.g., the second processor 1201' of the guidance device 105 as shown in FIG. 14, a processor of the system 2 or the system 2' as best seen in FIGS. 13 and 19-20, etc.).

Preferably, the second processor (also referred to herein as "the Second Processor") 1201' is connected to, and/or communicates with, a second wireless circuit (e.g., second wireless circuit 1205, 1212 as shown in FIG. 14, communication interface 1205 as shown in FIG. 19, network interface as shown in FIG. 20 (which may operate as a wired and/or wireless communication circuit), etc.) to enable communication between the first processor 1201 and the second processor 1201' to transfer information therebetween. In one or more embodiments, the second processor 1201' operates to do one or more of the following: read one or more positions from an encoder (e.g., the encoder sensor 203, the encoder sensor 203 based on interaction with the encoder scale 204, etc.); detect one or more errors of an encoder (e.g., the encoder sensor 203, the encoder sensor 203 based on interaction with the encoder scale 204, etc.) and/or the second processor 1201'; and control LEDs (see aforementioned discussion regarding LEDs, including, but not limited to, the LEDs 210 of FIG. 3, etc.).

In one or more embodiments, the guidance device 105 includes at least three LEDs to convey information to a user of the device 105. A center or middle LED may operate to indicate status information of the device 105 and/or the guidance status, and two other LEDs may indicate rotational direction for guidance. Various combinations of indicational patterns may be used for the LEDs. For example, in at least one embodiment, in a case where the center or middle LED is flashing, then the LED is indicating that an error occurred. In a case where the center or middle LED is "On", then one or more guidance features are enabled. In a case where the center or middle LED is "Off", then the one or more guidance features are disabled. In one or more embodiments, when one of the other two rotational direction LEDs is flashing, then that indicates guidance is occurring and that the user should change the insertion angle in one direction. In one or more embodiments, when a second of the other two rotational direction LEDs is flashing, then that indicates guidance is occurring and that the user should change the insertion angle in a second direction. When both of the two rotational direction LEDs are on, then the one or more guidance features are enabled, and the user should stop adjusting the insertion angle. When both of the two rotational direction LEDs are off, then the one or more guidance features are disabled. In one or more embodiments, a frequency of the flashing of one or more of the LEDs may be used, and may change depending on distance (angle) between a current position and a target position. For example, in at least one embodiment, when a distance (angle) is long, the frequency may be low, and when the distance (angle) is near/short, then the frequency may be high. Other modifications to the number of LEDs, frequency of the flashing, information conveyed via the LEDs and configuration of the LEDs may be made depending on the information that a user desires to receive from the device 105 (and construction of the device 105 may occur based on such specifications). The LEDs 210 may also be used to indicate whether the fiducial location is accurate or not, and may indicate to a user which way to move, guide or rotate the guidance device 105 to achieve accurate registration of the guidance device 105.

In one or more embodiments, the information transferred between the first processor 1201 and the second processor 1201' includes one or more of the following: a position detected from an encoder (e.g., the encoder sensor 203 as aforementioned; in one or more embodiments, the detected position may be an angle position), a status of an encoder (e.g., the encoder sensor 203), a status of the second processor 1201', a status of the first processor 1201, a target position based on a trajectory or trajectories, a status of the guidance device 105, and a signal to enable or disable one or more guidance features of the guidance device 105. In one or more embodiments, an enable signal for the guidance device 105 may not be needed in a case where reception of target position information enables the one guidance features, and, in one or more embodiments, a disable signal for the guidance device 105 may not be needed in a case where the second processor 1201' stops the one or more guidance features automatically. In one or more embodiments, the signal to enable or disable one or more guidance features may include a guidance completion signal or information to be transferred between the first processor 1201 and the second processor 1201'.

Additionally, information conveyed by one or more components, such as, but not limited to, one or more of the device 105, the computer 2, the system 10, the first and second processors 1201, 1201', etc., may depend on the desired specifications for the guidance device and/or system. For example, structural attributes (defining how such components are structurally built to achieve the desired functional behavior) may change depending on a desired medical procedure. For example, in one or more embodiments, the guidance device 105, the system 10 and/or one or more other components of the system 10 may be used for the medical procedure of ablating tumors in a patient body. Because tumors may be invisible, users may confirm where tumors are using the image scanner 5 (e.g., a CT scanner) or other scan devices. The computer 2, the guidance device 105, and/or the guidance system 10 calculates an insertion point, an insertion angle, a depth, an ablation time and an ablation power of candidate trajectories, and users of the system 10 may input such calculated results into the system 10 for needle guidance planning and/or performance and/or for visualization and manipulation of registration result(s). After a trajectory users choose is set to the guidance device 105, users may insert the needle 300 (best seen in FIG. 3; e.g., the needle may be for ablation in an ablation procedure, a biopsy procedure, etc.) with the guidance device 105 accurately.

In one or more embodiments, users may turn on the whole guidance system 10 including the guidance device 105 at first. The guidance system 10 may establish a wireless connection between the first wireless circuit 1205, 1212 and the second wireless circuit 1205, 1212 in a startup routine. Additionally or alternatively, a wired connection may be used.

After the preparation or the startup routine, a patient may be scanned by the image scanner 5 (e.g., the CT scanner 5 as shown in FIG. 14) with, or using, a disposable grid in one or more embodiments. The disposable grid operates to allow users find an insertion point more easily and more accurately. A disposable grid known to those skilled in the art may be used (such as, but not limited to, a Beekley Medical® Guidelines® CT Biopsy Grid 217, which may be obtained via Beekley Medical's website: https://www.beekley.com/Product-Details/GuideLines/CT-Biopsy-Grid-217). In one or more embodiments, users may use disposable fiducial markers (such as the aforementioned fiducial markers 209, fiducials F-1 through F-8, any of F-1 through F-8, etc.) instead of a disposable grid. Additionally or alternatively, users may find the insertion point without the grid and/or fiducial markers 209, F-1 through F-8, etc.

As aforementioned, in one or more embodiments, the first processor 1201 may load the scanned images, and may show the scanned images on the display 1209. A user or users of the system 10 may find a target region or regions from the scanned images and may set the target region or regions to the guidance system 10. The user or users may input data via one or more input devices (e.g., the keyboard 1210, the mouse 1211, etc.). Once settings and/or data are input, the first processor 1201 may then commence interaction for the needle guidance planning and/or performance.

After a user or users define an insertion point and make a trajectory, then the one or more users may put the guidance device 105 on or around the insertion point of the patient. The guidance device 105 may be fixed to the patient using any known methods or tools to those skilled in the art, including, but not limited to, using sticky tape. Thereafter, the patient may be scanned by the image scanner 5 (e.g., a CT scanner) with the guidance device 105 in place on the patient, and the registration result(s) may be determined and manipulated as needed to achieve accurate registration of the guidance device 105.

In one or more embodiments, at least the first processor 1201 registers the guidance device 105 and the scanned images using the fiducial markers 209, F-1 through F-8, any of F-1 through F-8, etc. The first processor 1201 is able to detect a position of the guidance device 105 in 3D space because the fiducial markers 209, F-1 through F-8, any of F-1 through F-8, etc. are placed in the fixed part or portion 205 of guidance device 105 (see e.g., FIGS. 1-4B). Alternatively or additionally, registration may be performed using the other structural configurations and/or methods discussed herein, or may be set by using data defining a predetermined location/position as aforementioned.

After the guidance device 105 is registered, the first processor 1201 may update the trajectory automatically to reduce error (or a user may update the trajectory manually via interaction with the first processor 1201 when desired). To avoid errors that may occur in a situation where a center of the guidance device 105 is different from a predefined insertion point, in one or more embodiments, the first processor 1201 may update the insertion point to set the center of the guidance device 105, and may calculate the insertion angle and depth thereafter.

In one or more embodiments, the first processor 1201 may send insertion angle information, and may enable a signal of one or more guidance features to the guidance device 105 (e.g., before the guidance device 105 beings to guide the one or more needles and/or other medical apparatus attached thereto for guidance). After the one or more guidance features of the guidance device 105 are enabled, the LEDs or other indicators of the device 105 may be lit or turned on to indicate information for the user or users. The guidance device 105 may begin guidance when target angle information is received. Then, an enable or disable signal may not have to be used in one or more embodiments as aforementioned.

Additionally, in one or more embodiments, the first processor 1201 may reconstruct an oblique image based on loaded images and angle information. The first processor 1201 may show the image on the display 1209, and may update the displayed image to be synchronized with new angle information.

In a case where the medical procedure is ablation for example, the method(s) may include one or more ablation planning and performance steps, including, but not limited to, one or more of the following: (i) loading images (e.g., from a scanner, a PACS or other scanning device/system, or using a fresh or newly scanned image) (see step S1 in FIG. 15); (ii) visualizing images (e.g., such as by showing multiple panes (views, such as, but not limited to, axial, coronal, sagittal, 3 dimensional (3D), etc.) (e.g., each view may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by moving at least one line (e.g., an axis or axes) to cut through one or more planes to reformat a 3D data set and display the reformatted slices in the 3D view; etc.)) (see step S2 in FIG. 15); (iii) identifying a treating zone or target (e.g., a lesion or tumor) (see step S3 in FIG. 15); (iv) defining a target point, an entry point and a trajectory between the target and entry points (see step S4 in FIG. 15) (as shown in step S4*b*, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 15). Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). In one or more embodiments of the present disclosure, a method is provided to determine or suggest a target point or points that is clinically the best choice (e.g., mathematically, statistically, etc.) for placement of the target point(s). In one or more embodiments, target point(s) may be determined by finding or determining a medial axis or center line of the target or treating zone (see step S4 of FIG. 15).

Figure 15:
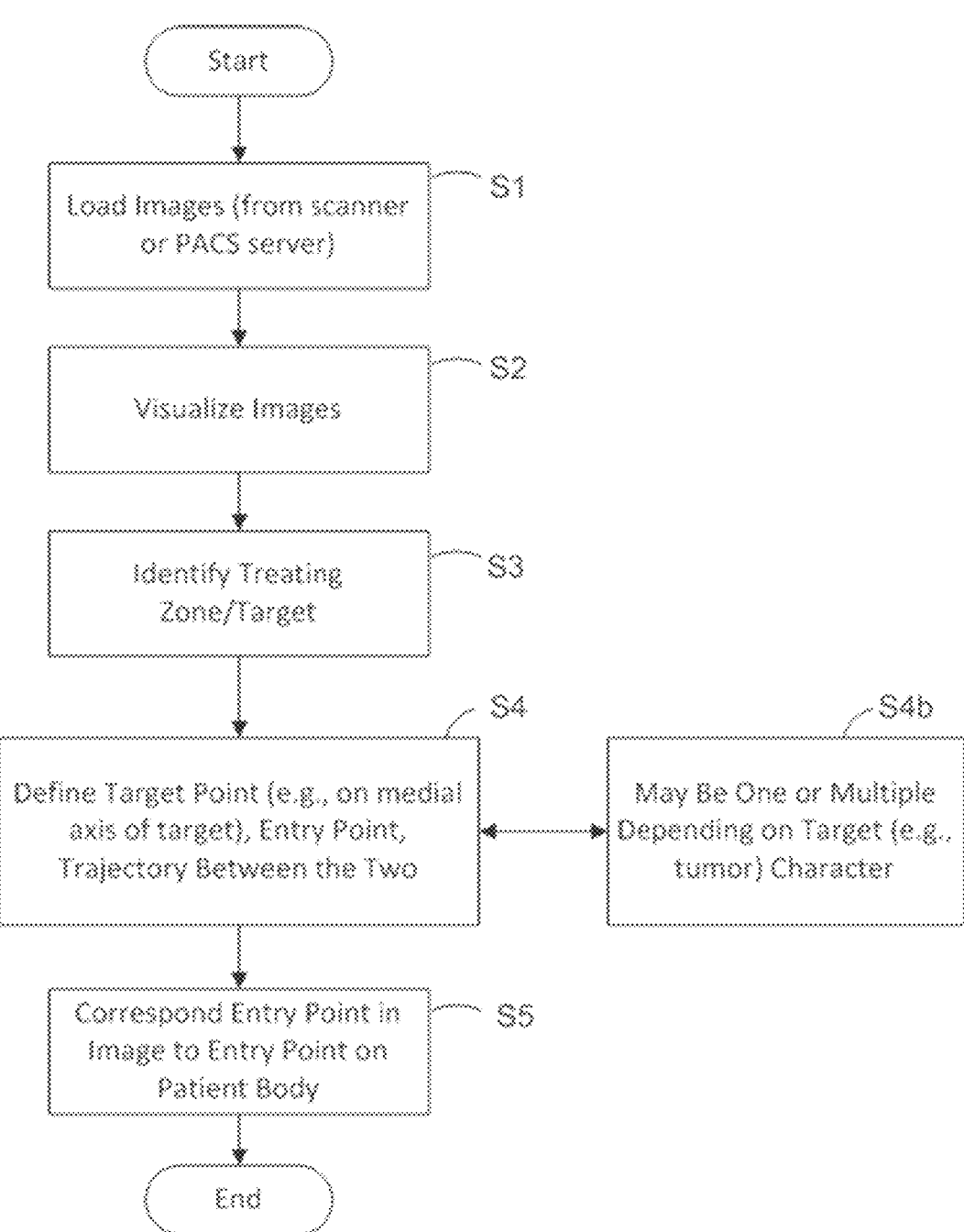
FIG. 15 is a flow chart showing at least one embodiment of a method for performing ablation and/or needle guidance planning and/or performance in accordance with one or more aspects of the present disclosure.
Figure 16:
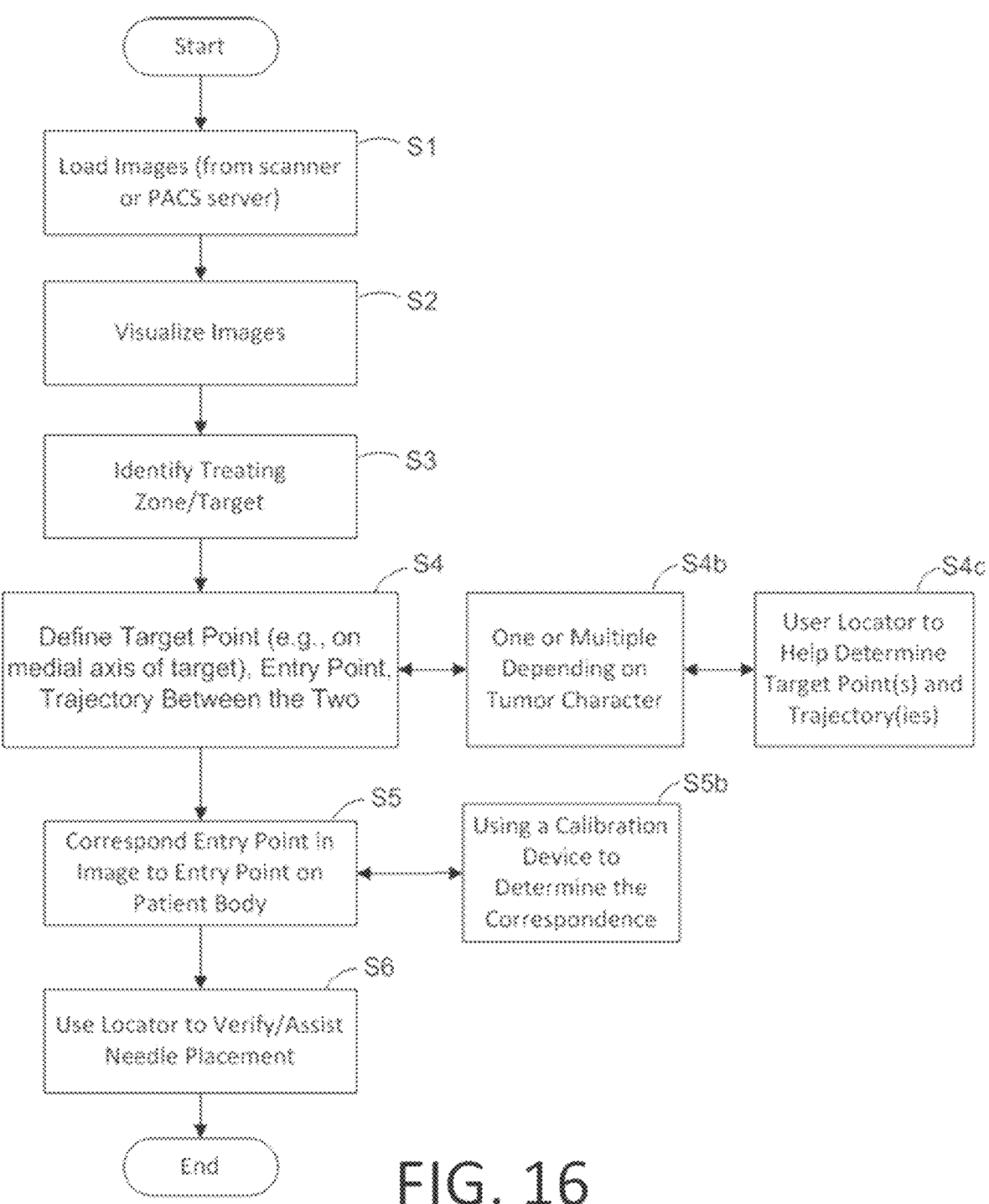
FIG. 16 is a flow chart showing at least another embodiment of a method for performing ablation and/or needle guidance planning and/or performance in accordance with one or more aspects of the present disclosure.

For any identification of a target or targets step(s) discussed herein (such as, but not limited to, step S3 of FIGS. 15-16; step(s) S4, S4*b* of FIG. 15; step(s) S4, S4*b*, S4*c* of FIG. 16; etc.), any method of identifying a target biological object or zone, including those known to those skilled in the art, such as a clinician, and including the additional method(s) provided herein, may be employed. For example, in one or more embodiments, a target zone and target points are to be identified. A target zone may be identified by an image segmentation method(s). Clinicians may initially define a few points, called seeds, which may or may not be the target points within an identified target region, such as a lesion or tumor region. In one or more embodiments, an active contour model, such as a snake algorithm (see e.g., one example explained by C. Xu and J. L. Prince in "Gradient Vector Flow: A New External Force for Snakes", Proc. IEEE Conf. on Comp. Vis. Patt. Recog. (CVPR), Los Alamitos: Comp. Soc. Press, pp. 66-71, June 1997), may be used to iteratively determine a boundary of the target region. The initial seeds may not converge to a true boundary quickly, so, in one or more embodiments, a watershed method (see e.g., one example explained by Gouze A., De Roover C., Herbulot A., Debreuve E., Barlaud M., Macq B. in "Watershed-driven Active Contours for Moving Object Segmentation", in Proceedings of IEEE International Conference on Image Processing (ICIP), vol. II, pp 818-821, Genova, Italy, September 2005) may be used together with the snake algorithm to make the segmentation smoother and faster. Compared to manually drawing a boundary of a target region, such as a lesion or tumor region, such a method or methods generate a far more accurate and consistent boundary, which may be used to determine a volume of a target (e.g., a tumor or lesion) and may be used in a later stage for quantitatively characterizing the tumor or lesion and assessing ablation results. The resulting boundary forms a target zone.

Additionally or alternatively, one or more method(s) of the present disclosure may further include performing ablation planning and/or performance with the guidance device 105 as shown in FIG. 13. In addition to the steps shown in FIG. 15 (the details of which are aforementioned and will not be repeated herein accordingly), such one or more method(s) employing a guidance device, such as the guidance device 105 may further include, but are not limited to, one or more of the following: (i) using a guidance device, such as the guidance device 105, to help determine the target point(s) and trajectory(ies) in steps S4 and/or S4*b* (see also steps S4, S4*b* and S4*c* in FIG. 16); (ii) using a calibration device (e.g., such as, but not limited to, fiducial markers (e.g., the fiducial markers 209, the fiducials F-1 through F-8, any of the fiducials F-1 through F-8, etc.), systems and methods of registration, such as those disclosed in U.S. patent application Ser. No. 14/755,654 and published in U.S. Pat. Pub. No. 2017/0000581, which are incorporated by reference herein in their entireties) to determine or assist with the correspondence step of S5 (see also steps S5 and S5*b* in FIG. 16); and (iii) using a guidance device, such as the guidance device 105, to verify and/or assist with needle placement when performing ablation for the patient (see step S6 in FIG. 16). In one or more embodiments of the present disclosure, at least one embodiment of a method for performing ablation planning or ablation performance is to use such calibration device(s) and/or locator device(s) to increase or maximize the success of the ablation procedure depending on one or more variables, such as, but not limited to, needs of the patient, characteristics of the lesion/tumor, if movement of the patient is needed during the procedure, etc. In one or more embodiments of the present disclosure, such calibration device(s) and/or locator device(s) assist a clinician in finding a medial axis or center line of the target biological object, such as a lesion or tumor.

In one or more embodiments, workflow for a particular procedure, such as guidance planning and/or performance and/or ablation planning and/or ablation performance, may be combined with segmentation, registration and differential image view steps to provide better differential images (such as, but not limited to, segmentation, registration and differential image steps disclosed in PCT/US2018/020752, which is incorporated by reference herein in its entirety) and the manipulation of registration result(s) as discussed herein, which avoid the generation of misleading artifacts in images and/or avoid other issues with procedure-related problems. Differential images are a quick way to give clinicians feedback of needle guidance and/or ablation results. While thermal maps may be used in one or more embodiments, such thermal maps may be affected by environmental changes, such as blood flow, and measurements may not be easily localized depending on the circumstances. Various types of ablation may be used in one or more embodiments (e.g., cryoablation, microwave ablation, laser ablation, etc.). While cryoablation may be used, iceballs may form, and are very visible under MRI. Ultrasound may be used in one or more of the methods discussed herein for navigation, and some indication of an ablation result may be obtained from the same tool. However, ultrasound images may be noisy and may be hard to quantitatively measure. Regardless of which detection or monitoring tool/technique is employed, the integration of the workflow with segmentation, registration and differential image view steps reduces and/or avoids such issues to provide a useful differential image or images for clinicians to use in one or more procedures (e.g., ablation, radiotherapy, etc.).

For medical procedures, such as ablation, one probe ablation or multi-probe ablation may be performed. For multi-probe ablation, serial or parallel multi-probe ablation may be performed. In serial ablation, ablation is done in sequence of one probe being inserted, ablated, confirmed, then another probe being inserted, ablated, confirmed, and repeating such steps if more probes are needed. In parallel ablation, all probes are inserted before ablation starts. Clinicians may decide which ablation approach is chosen. No matter which approach is chosen, a confirmation stage is needed after the ablation is done. Based on information from each confirmation, a clinician may determine whether additional ablation is needed, and, if so, where to plan for the next probe to be used. Confirmation also provides clinicians with an indication as to whether the margin is reached or overreached to evaluate the results of the ablation procedure.

To aid clinicians in performing confirmation steps, one or more embodiments of the present disclosure may include confirmation with margin view so that confirmation or any other determination process requiring clear image feedback may be performed more effectively (such as, but not limited to, confirmation steps disclosed in PCT/US2018/020752, which is incorporated by reference herein in its entirety). While quantitative measure of coverage is useful, a visual quick assessment is also very useful in one or more applications. The margin view gives a better view than the common overlay of before and after ablation images to more easily and effectively determine the success of the ablation process. In one or more embodiments, the target(s), such as lesion(s) or tumor(s) may be segmented before and after ablation occurs, and differentiation between the two sets of segmented target images may be determined. Thereafter, the differential may be overlaid on the after-ablation images to evaluate the ablation process. Additionally or alternatively, one or more method(s) of the present disclosure may further include performing ablation planning and/or performance with the guidance device 105 as shown in FIG. 13 and in FIGS. 15-16. One or more embodiments of methods for evaluating or determining a margin view may include, but are not limited to, one or more of the following: (i) loading images (e.g., from a scanner, a PACS or other scanning device/system, or using a fresh or newly scanned image) (see step S1 in FIGS. 15-16); (ii) visualizing images (e.g., such as by showing multiple panes (views) (e.g., each view may represent a different aspect of the image); as described above for step S2 in FIGS. 15-16; (e.g., in medical image software, such as, for example, the application shown in PCT/US2018/020752, which is incorporated by reference herein in its entirety); as otherwise described herein; etc.) (see step S2 in FIGS. 15-16); (iii) performing device registration (also referred to herein as device calibration) to make a correct correspondence or alignment between an image and real world dimensions for a patient (see e.g., steps S5 and/or S5*b* of FIG. 15 and/or FIG. 16 which may be incorporated into or used as a configuration or registration step; see also, device registration as discussed in PCT/US2018/020752, which is incorporated by reference herein in its entirety; see also, aforementioned registration with masking processes/steps (such as, but not limited to, the steps shown in FIGS. 1A-12); (iv) identify a target or target(s), such as a zone or biological object (see step S3 of FIGS. 15-16); (v) segmenting the identified targets (at one reference point in the planning or procedure (e.g., before moving a needle, before performing ablation, before performing the next iterative or incremental planning step (either during the procedure or in simulation or planning), before moving a patient, etc.)—also referred to herein as "targets (1)", i.e., the targets identified at stage (1)); (vi) performing an incremental planning or performance step (e.g., move a needle, insert a new probe or needle, perform ablation, perform the next planning step, moving a patient, etc.); (vii) re-scanning the targets or obtaining newly scanned images of the targets after performing the incremental planning or performance step; (viii) visualizing images (e.g., such as by showing multiple panes (views) (e.g., each view may represent a different aspect of the image); as described above for step S2 in FIGS. 15-16; as otherwise described herein; etc.)); (ix) identifying a target or target(s), such as a zone or biological object (which may be the same or similar to step S3 of FIGS. 15-16 such that the above details regarding same are not repeated herein); (x) segmenting the re-scanned targets (at a second reference point in the planning or procedure (e.g., after moving a needle, after moving or adding a probe, after performing ablation, after performing the next iterative or incremental planning step (either during the procedure or in simulation or planning), etc.)—also referred to herein as "targets (2)", i.e., the targets as re-scanned at stage (2) after stage (1)); (xi) performing image registration (e.g., before conducting differentiation of current images and previous images); (xii) performing differentiation of current images (e.g., images of stage (2)) and previous images (e.g., images of stage (1)) to enhance the view of the effect of the procedure (e.g., ablation (especially when using microwave or radiofrequency (RF) ablation (in one or more embodiments, differentiation subtraction may not be needed for cryoablation)), radiotherapy, etc.); and (xiii) overlaying the differential on the current images (e.g., images of stage (2)). Image segmentation and registration may be performed using any method known to those skilled in the art, such as a clinician, and may be performed using the aforementioned registration result(s) visualization and manipulation steps.

The image differentiation may be used to enhance the visualization of a needle (or other medical device) guidance result and/or an ablation result, monitor probe progression during insertion, or to track any other incremental step in a procedure (e.g., ablation, radiotherapy, etc.). By way of example, a concept of such an enhancement after performing ablation is shown in PCT/US2018/020752, which is incorporated by reference herein in its entirety. The target or target zone of a biological object (such as a lesion or tumor) is surrounded by an ablation zone or ablated zone (once ablation is performed). As such, in one or more embodiments, such as when performing differentiation and overlaying the differential on the current image(s) of stage (2) or final images, a margin map is formed. The margin map may be used by a clinician to determine whether or not to edit a procedure plan and/or to evaluate whether the plan or procedure is optimal (e.g., the best option available) or has been successful (and to gauge how successful). This improved ability to measure success is good for feedback (such as for the clinician, patient, hospital, other clinicians consulting such results, etc.), and provides an outcome oriented application in one or more embodiments of the present disclosure. For example, the percent of the margin (and/or other metrics of the margin) may be used to indicate how well the procedure went. A minimum or a maximum of the margin view or map may be set or predetermined by a clinician. The treatment or target zone may be displayed, overlaid on the target zone or target object (segmented), e.g., a tumor or lesion.

Additionally or alternatively, clinicians may perform simulations with one or more embodiments of the planning methods/software of the present disclosure to create an optical plan, to accommodate one or more variables (e.g., patient movement during the procedure, tissue deformations, etc.), and to evaluate the potential outcome. By way of at least one example, a simulation of a target zone (e.g., in an example where the medical procedure is ablation, the simulation may be an ice ball for cryoablation, a balloon for microwave ablation, etc.) may be conducted. By way of another example, a simulation may be performed to mimic tissue deformation. For example, if clinicians segmented an organ or tumor (suppose an oval shape for purposes of the example simulation), the medial axis algorithm may take the segmented object as input and generate a medial axis output (typically it is a curve), which may be overlaid on the segmented object. By dragging and manipulating the medial axis curve, the curve may change its shape and location in space. Due to the fact that a volume may be reconstructed from a medial axis curve, the deformation may be simulated or obtained by dragging and manipulating the medial axis.

One or more embodiments of the guidance planning and performance and/or visualization and manipulation of registration result(s) apparatuses and systems, and methods and storage mediums of the present disclosure may operate to reduce the number of iterations for the determination of the insertion point(s) and trajectory of the needle(s) and/or probe(s) after being inserted into the entry point(s), especially due to the improved and efficient registration method(s) discussed herein. This is beneficial for reducing exposure to radiation when dealing with CT scans and reduces the total time of scanning when dealing with any type of scan, including, but not limited to, CT, MRI or otherwise. In one or more embodiments, registration with fiducial markers (such as a sticker grid as aforementioned, the fiducial markers 209, any or all of fiducials F-1 through F-8, etc.) may be used on the patient at or near an insertion point before conducting a CT/MRI scan. This registration step helps to accurately correlate physical dimensions to what to see in the scanned images.

After a target zone is identified, clinicians may pick up a point or a few points within the target zone as target point(s). From there on, in the case of ablation, an ablation zone (for example iceball) may be defined on or around the target zone (e.g., in the case of the iceball example, the ball may be centered on the ablation zone). In other medical procedures, a guidance zone for one or more needles may be more generally defined on or around the target zone.

While clinicians may pick target points by trial and error, such trial and error leads to inefficiencies, such as, but not limited to, longer procedure time, more invasive and repeated steps (e.g., needle or probe insertion/movement), lack of accuracy, etc.

Figure 17:
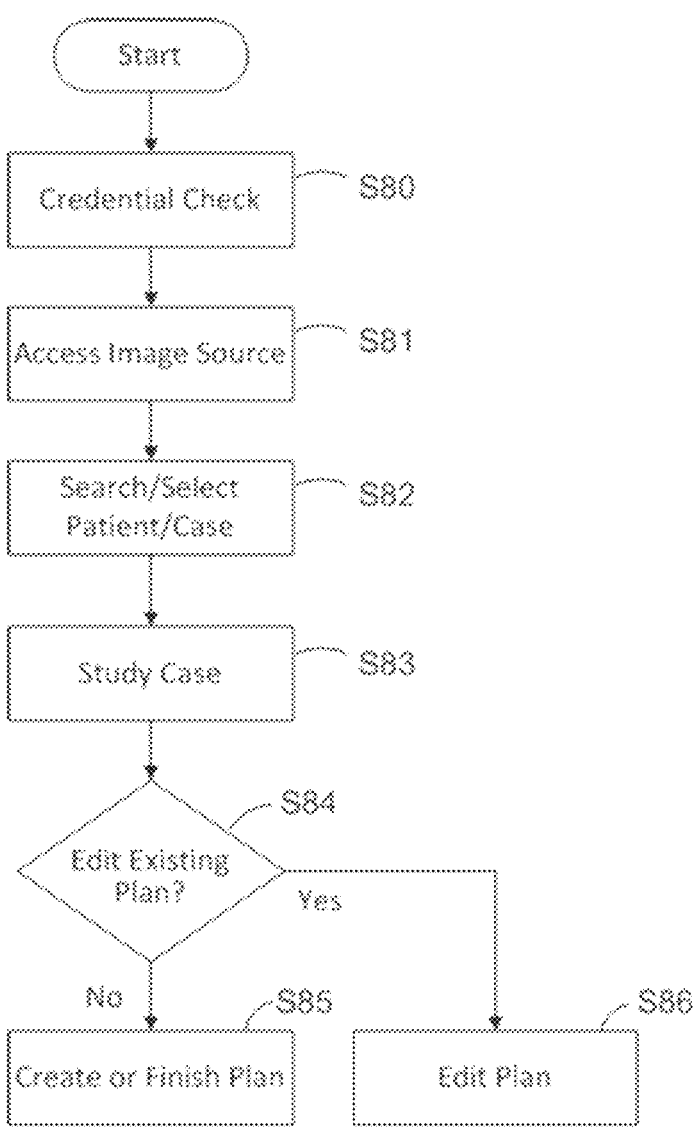
FIG. 17 is a flow chart showing at least another embodiment of a method for performing a medical procedure (e.g., ablation and/or needle guidance planning and/or performance) using a security or credential check in accordance with one or more aspects of the present disclosure.

Additionally, in one or more embodiments, a security check may be included to perform the check in the surgical room prior to the needle guidance planning and/or procedure to ensure maximal security and safety. To make the security check convenient for clinicians (who have scrubbed in and are wearing gloves at that point and may not be able to use their hands for performing the security check), iris and/or face recognition may be incorporated. Such iris and/or face recognition based approaches may be preferred to control access to patient data (CT scan for example) and communication with peers. While other forms of security control may be used, forms, such as, but not limited to, typing a password, finger print scan, or other forms that require the use of a clinician's hand(s), may not be preferred because a clinician's hand(s) may be sterilized. Once logged in, clinicians may be able to access patient data and communication with peers. FIG. 17 depicts where this checking step may be employed for access image data to create or edit a plan for any medical procedure, such as ablation, cryotherapy, biopsy, etc. For example, prior to any method disclosed herein for performing needle guidance planning and/or performance or ablation planning and/or performance, the credential check (step S80 of FIG. 17) may be performed to make sure that the clinician is permitted to access patient data and communication with other clinicians. Once the clinician passes the credential check (S80), then the clinician has access to the image source (see step S81 of FIG. 17), and may search or select a patient or case file (see step S82 of FIG. 17). Once the patient or case file is retrieved in step S82, the clinician may study the case (see step S83 of FIG. 17), and may determine whether edit(s) to an existing procedure plan (e.g., an ablation plan, a radiotherapy plan, a biopsy plan, needle guidance plan, etc.) are required or not (see step S84 in FIG. 17). If "No" edits to an existing plan are needed (e.g., a plan is finished, a plan does not exist, etc.), the clinician may create or finish a plan for the procedure (see step S85 of FIG. 17). If "Yes" and edits to an existing plan are needed, the clinician may edit the previously created plan (see step S86 of FIG. 17). These steps may be used in addition to any of the aforementioned methods for performing guidance planning and/or performance, for ablation planning and/or ablation performance, for radiotherapy planning and/or performance, for guiding multiple needles or multiple ablation probes, for visualizing and manipulating registration result(s), or other procedural methods as may be useful.

Figure 18:
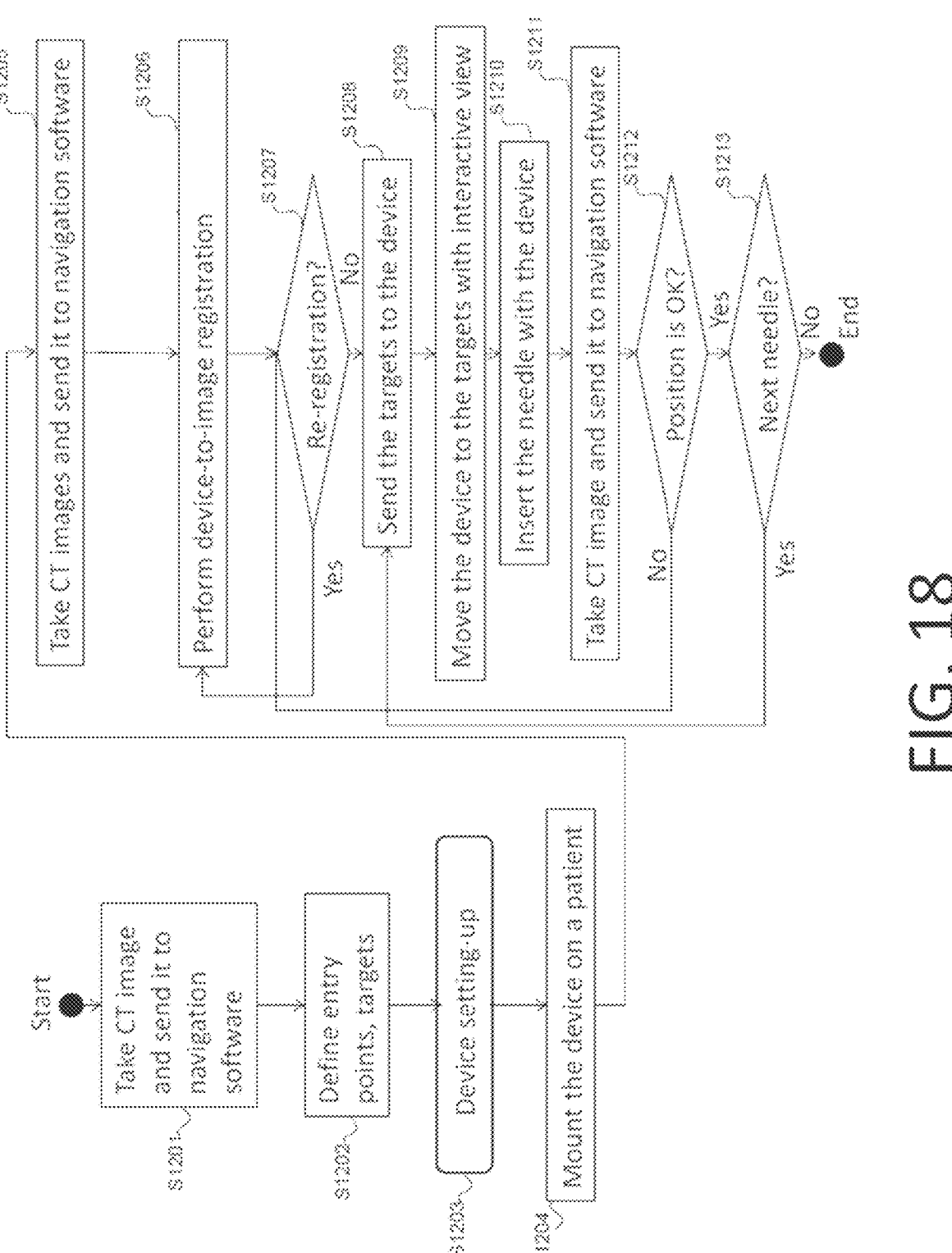
FIG. 18 is a flow chart illustrating a process for guidance of a needle using a medical guidance device and/or system in accordance with one or more aspects of the present disclosure.

FIG. 18 is a flowchart illustrating a process for guidance of a needle or needles using the medical guidance device 105. In step S1201, an operator takes medical images using the medical imaging device 5. The medical imaging device 5 is a CT scanner in this particular embodiment, and sends the CT images to the first processor 1201 of the computer 2 as aforementioned.

At step S1202, with the CT images, the operator defines targets for percutaneous intervention with a needle-like medical tool and the skin entry point. At the same time, by connecting the target to the skin entry point, the operator can determine the plane for the trajectory of insertion of the needle-like medical tool using at least the first processor 1201 (and any images and/or software displayed on the aforementioned display 1209 of the computer 2). Also, in this step, the operator marks the skin entry point on the patient using, for example, grid visible markers on the patient as aforementioned.

In step S1203, the operator sets up the system 10, including the device 105, to calibrate the system 10 and/or one or more components thereof, and sets a proper initial state of the medical guidance device 105. Additionally, the first processor 1201 may set up, synchronize and/or otherwise figure out the orientation, for example, between the encoder sensor 203 and the encoder scale 204.

After the setting up the device 105, in Step S1204, the operator mounts the medical guidance device 105 onto the patient aligning a predetermined portion (e.g., a center) of the device 105 to the skin entry point. When an adhesive marker is being utilized, the operator may align a center marker to the skin entry point and then adhere the medical guidance device 105 in place via an adhesive. In one or more embodiments, the user then may remove a peel-away portion of the adhesive marker to expose the patient's skin.

In Step S1205, after the device mounting, the user takes images (e.g., CT images) including the medical guidance device 105 and sends the CT images to the first processor 1201 (and related navigation or guidance software for processing the data as needed). Using the CT images with the medical guidance apparatus 105 showing, in Step S1206, the user conducts device-to-image registration. In this step, the first processor 1201 (e.g., using guidance or navigation software) recognizes the position and orientation of the medical guidance device 105 on the patient in the CT images, i.e., in the coordinate of the CT image, by using fiducial markers (e.g., the fiducial markers 209, any or all of fiducials F-1 through F-8, etc.) or fiducial markers located on the corners of the fixed portion 205. This fiducial marker detection may be manually performed by user instruction with a user interface or, may be fully automated by using a computer algorithm via the first processor 1201 and/or the second processor 1201', such as, but not limited to, the aforementioned registration with masking processes/steps/algorithms (see e.g., FIGS. 1A-12). The detected fiducial markers are compared with the designed geometrical configuration of the fiducial markers in the medical guidance device 105, then the first processor 1201 and/or the second processor 1201' (e.g., using guidance or navigation software) may recognize the position and the orientation of the medical guidance device 105 in CT images. The navigation software may also reflect the plan of the trajectory with two device parameters, which are angular position of the moveable portion 206

$$206 \ (\theta_E^F)$$

and insertion angle on the guide of the arc member 207 and/or the arc member 207

$$207 \ (\theta_E^F)$$

at this step.

In step S1207, the user may be asked whether the device-to-image registration is appropriate or not by the first processor 1201 and/or the second processor 1201' (e.g., via the navigation software displayed on the display 1209). This step may correspond to or include aforementioned steps S109 through S112. If not ("No" in Step S1207 or "NO" in step S109), the operator may conduct Step S1206, and/or aforementioned steps S110 through S104-S108, to perform the device-to-image registration again.

If the device-to-image registration is appropriate ("Yes" in Step S1207 or "YES" in S111), flow proceeds to Step S1208 or step S112 where the user may send the target device parameters $$\theta_E^F, \theta_P^{MR}$$

to the first processor 1201 and/or the second processor 1201' (e.g., by registering the device space to image space).

Afterwards in Step S1209, the operator may manually rotate the arc member 207 via the moveable portion 206 of the device 105 while the first processor 1201 and/or the second processor 1201' (e.g., using guidance or navigation software) interactively updates the cross-sectional image on the guide surface by using the real-time angular position of the movable portion 206. Also, the first processor 1201 and/or the second processor 1201' may compare the real-time angular position of the moveable portion 206 with the target angular position. Once the moveable portion 206 reaches the target angular position, the first processor 1201 and/or the second processor 1201' indicates the end of targeting of the moveable portion 206 of the device 105. Then, the first processor 1201 and/or the second processor 1201' (e.g., via guidance or navigation software displayed on the display 1209) informs the user of the end of targeting or guidance.

Upon establishing the target angular position of the moveable portion 206 of the device 105, in Step S1210, the user picks the specific angular reference mark (or other indicator mark being used in any particular embodiment) indicated by the target insertion angle on the arc 207 of the device 105 and with the specific angular reference mark (or other indicator), the user inserts the needle-like medical tool from the skin entry point to the target. In the case of the medical guidance apparatus device 105 (see various embodiment examples in at least FIGS. 2-9 and 13-14), the operator may slide the needle-like medical tool along the guide surface of the arc 207 (see FIGS. 2-9) until reaching the appropriate reference mark (or other used marker). In doing so the user may apply force. However, due to the structural advantages discussed above provided by the closed/monolithic structure of the guide and/or of the movable portion 206 of the device 105, the arc portion 207 is able to fully support the force without deflection or bending. Variations may be made to the device 105 in accordance with one or more features of the present disclosure. For example, other types of guidance devices 105 may be used, such as those discussed in U.S. Provisional Patent Application No. 62/764,849, filed on Aug. 15, 2018, the entirety of which is incorporated by reference herein, and/or as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties.

In Step 1211, after the first attempt of the insertion, the user takes CT images of the inserted needle-like medical tool, the medical guidance device 105, and the CT images and sends them to the first processor 1201 and/or the second processor 1201' (and any guidance or navigation software being used). With the CT images of the inserted needle-like medical tool, the user evaluates the position of the inserted needle-like medical tool.

In step S1212, the position of the inserted needle-like medical tool is checked and if the user thinks the position is suboptimal ("No" in Step S1212), flow proceeds back to Step S1208 where the user can update the trajectory to improve the position of the needle-like medical tool with the first processor 1201 and/or the second processor 1201' (e.g., by using guidance or navigation software such as discussed in U.S. Provisional Patent Application No. 62/764,849, as discussed in U.S. Provisional Patent Application No. 62/875,243, as discussed in U.S. Provisional Patent App. No. 62/764,820, and/or as discussed in U.S. patent application Ser. No. 16/539,769, the applications of which are incorporated by reference herein in their entireties). At the same time, with the latest CT image, the user finds the dislocation of the target, skin entry point and the medical guidance device 105 and updates the registered position and orientation of the medical guidance device 105. Thus, the user can conduct the device-to-image registration with the latest CT images. By updating the device-to-image registration in this way and/or using the aforementioned method steps (see e.g., FIGS. 1A-12 and related discussions), the user can reduce discrepancy of the actual geometrical relationship between the medical guidance device 105 and the target. Specifically, since the medical guidance device 105 is mounted on the patient and can move with the patient body together, the update of the device-to-image registration can effectively compensate rigid dislocation of the patient from the older CT images.

With updated plane of the trajectory and the device-to-image registration, the user can perform another attempt of the insertion with the same steps as in the first attempt.

In step S1212, if the position of the inserted needle-like medical tool is checked and the user is satisfied with the results ("Yes" in Step S1212), flow continues to Step S1213. In Step S1213, a determination is made as to whether insertion of another needle-like medical tool is needed. If insertion of another needle-like medical tool is needed ("Yes" in Step S1213) flow returns back to Step S1205. If insertion of another needle-like medical tool is not needed ("No" in Step S1213) flow is complete. When inserting another needle-like medical tool, the user may decouple the guide or the movable portion 206 from the fixed portion 205 as necessary without needing to unmount the fixed portion 205 of the aforementioned embodiment examples of the device 105. In the case of inserting another needle-like medical tool in another guide, preferably the user may remove the previous needle-like medical tool from the instrument holder 70.

Once all of the needle-like medical tools have been inserted, the operator may decouple the guide or the arc 207 from the moveable portion 206. Once the guide or the arc 207 has been decoupled and can be freely lifted away, the operator may orient the guide such that each of the needle-like medical tools passes through the gap or opening of the guidance device 105. Thus, the guide may be completely removable from the procedure site, even when the needle-like medical tool is tethered, such as for percutaneous ablation probes. Similarly, one or more portions of the other embodiments of the device 105 may be removed as needed (e.g., the movable portion 206) as aforementioned.

In at least one embodiment, the computer 2, 2' operates to control the medical procedure (e.g., needle guidance, ablation, biopsy, etc.) planning and/or performance, probe or needle guidance planning and/or performance, and/or visualization and manipulation of registration result(s) device(s), system(s) and/or storage medium(s), and may display the scanned image(s) and the procedure plan (e.g., on a monitor or screen such as a display, screen or monitor 1209 as shown in the computer 2 of FIG. 13, in the computer 2 of FIG. 19 and/or the computer 2' of FIG. 20 as further discussed below). The console or processor 2, 2' (or the first processor 1201 of the console or computer 2, 2') or the second processor 1201' of the device 105 may be used to control any portions of the system 10 of FIG. 13, for example, including, but not limited to, the medical device 1, the guidance device 105, the PACS system 4, the image scanner and console 5 (e.g., CT scanner), etc. The processor 1201 of the console 2, 2' and/or the second processor 1201' of the device 105 may be used to perform any of the aforementioned method(s) or algorithm(s), and may use one or more feature(s) of such method(s) or algorithm(s) in any combination desired by a clinician for a predetermined procedure (e.g., medical procedure (e.g., ablation, biopsy, etc.) planning and/or performance; needle or probe guidance; a combination thereof; etc.). For example, the CPU 1201 of the processor 2, 2' may load images (e.g., from a scanner or PACS 4) in step S1 of FIGS. 15-16 (see also, steps S800 in FIGS. 8 and 10-12), and may display such images to allow the clinician to visualize the images (e.g., in step S2 of FIGS. 15-16; see also, steps S800 in FIGS. 8 and 10-12). The computer, such as the console or computer 2, 2', may receive data from a device (e.g., such as the guidance device 105, an image scanner 5, a PACS 4, etc.) or a system via a network interface (see e.g., communication interface 1205 and network 1206 as shown in FIG. 19 or Network I/F 1212 as shown in FIG. 20), or the computer, such as the console or computer 2, 2', may obtain a set of imaging conditions using the operation input from the mouse or keyboard (see e.g., the keyboard 1210 as shown in FIG. 19 or the mouse 1211 and/or keyboard 1210 as shown in FIG. 20).

Unless otherwise discussed herein, like numerals indicate like elements. For example, while variations or differences exist between the methods, devices, systems or storage mediums, such as, but not limited to, the system 10, the communication devices and methods shown in FIGS. 1A-20, etc., one or more features thereof may be the same or similar to each other, such as, but not limited to, the use of one or more component(s) thereof (e.g., the console 2, the console 2', the medical device 1, the guidance device 105, the PACS 4, the CT scanner 5, any or all of the components of the figures, such as, but not limited to, those shown in FIGS. 1A-9, FIGS. 13-14, FIGS. 19-20, etc.). Those skilled in the art will appreciate that the method steps disclosed herein may operate in the same or similar fashion to those like-numbered elements of one or more other methods or algorithms as discussed herein. Those skilled in the art will appreciate that alternative embodiments of the system 10, may be used while having other variations as discussed herein for performing one or more methods discussed herein. Likewise, while the console or computer 2 may be used in one or more systems or with one or more methods disclosed herein, one or more other consoles or computers, such as the console or computer 2', may be used additionally or alternatively.

There are many ways to plan for and perform a medical procedure (e.g., needle guidance, ablation, biopsy, visualization and manipulation of registration result(s), etc.) or any other measurement or determination discussed herein, digital as well as analog. In at least one embodiment, a computer, such as the console or computer 2, 2', may be dedicated to control and monitor the devices, systems, methods and/or storage mediums described herein.

The electric signals used for imaging may be sent to one or more processors, such as, but not limited to, a computer or processor 2 (see e.g., FIGS. 13 and 19), the first and second processors 1201, 1201' (see e.g., FIG. 14), a computer 2' (see e.g., FIG. 20), etc. as discussed further below, via cable(s) or wire(s), such as, but not limited to, the cable(s) or wire(s) 113 (see FIG. 19). Additionally or alternatively, the electric signals, as aforementioned, may be processed in one or more embodiments as discussed above by any other computer or processor or components thereof. The computer or processor 2 as shown in FIGS. 13 and 19 may be used instead of any other computer or processor discussed herein (e.g., computer or processors 1201, 1201', 2', etc.), and/or the computer or processor 2, 2' may be used instead of any other computer or processor discussed herein (e.g., computer or processor 1201, 1201', etc.). In other words, the computers or processors discussed herein are interchangeable, and may operate to perform any of the multiple imaging modalities feature(s) and method(s) discussed herein, including using, controlling, and changing a GUI or multiple GUI's.

Various components of a computer system 2 (see e.g., the console or computer 2 as shown in FIG. 13) are provided in FIG. 19. A computer system 2 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 13). In addition, the computer system 2 may comprise one or more of the aforementioned components. For example, a computer system 2 may include a CPU 1201, a RAM 1203, an input/output (I/O) interface (such as the communication interface 1205) and a bus (which may include one or more lines 1213 as a communication system between components of the computer system 2; in one or more embodiments, the computer system 2 and at least the CPU 1201 thereof may communicate with the one or more aforementioned components of an ablation performance and/or planning and/or needle or probe guidance device or system, such as, but not limited to, the system 10 discussed herein above, via one or more lines 1213 or wirelessly through a first wireless circuit 1205, 1212 and a second wireless circuit 1205, 1212, and/or through communication or network interfaces that include wired and wireless structural attributes and features), and one or more other computer systems 2 may include one or more combinations of the other aforementioned components. The CPU 1201, 1201' is configured to read and perform computer-executable instructions stored in a storage medium. The computer-executable instructions may include those for the performance of the methods and/or calculations described herein. The system 10 may include one or more additional processors in addition to CPU 1201, and such processors, including the CPU 1201, may be used for performing ablation planning and/or performance and/or multiple needle or multiple ablation probe guidance. The system 10 may further include one or more processors connected via a network connection (e.g., via network 1206). The CPU 1201 and any additional processor being used by the system 2 or the system 10 may be located in the same telecom network or in different telecom networks (e.g., performing needle guidance, medical procedure (e.g., ablation, biopsy, etc.) planning and/or performance technique(s) may be controlled remotely or wirelessly).

The I/O or communication interface 1205 provides communication interfaces to input and output devices, which may include the medical device 1, the guidance device 105, the PACS 4, the CT scanner 5, a microphone, a communication cable and a network (either wired or wireless), a keyboard 1210, a mouse (see e.g., the mouse 1211 as shown in FIG. 20), a touch screen or screen 1209, a light pen and so on. The Monitor interface or screen 1209 provides communication interfaces thereto.

Any methods and/or data of the present disclosure, such as the methods for performing ablation planning and/or performance, radiotherapy, guidance of needle(s) and/or probe(s), visualization and manipulation of registration result(s) or otherwise as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 20), SRAM, etc.), an optional combination thereof, a server/database, etc. may be used to cause a processor, such as, the processor or CPU 1201 of the aforementioned computer system 2 and/or the system 10, the second processor 1201' of the device 105, etc., to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 2, the processor 1201' of the device 105, etc., as described above may be achieved utilizing suitable hardware, such as that illustrated in the figures. Functionality of one or more aspects of the present disclosure may be achieved utilizing suitable hardware, such as that illustrated in FIGS. 1A-20. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201, 1201' (e.g., as shown in FIGS. 14, 19 and/or 20) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 2' is shown in FIG. 20. The computer 2' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 2' includes a display 1209. The computer 2' may connect with the medical device 1, the guidance device 105, the PACS 4, the CT scanner 5, communication devices (e.g., to discuss the procedure with peers, clinicians, etc.) via the operation interface 1214 or the network interface 1212 (e.g., via wired or wireless connection). The operation interface 1214 is connected with an operation unit such as a mouse device 1211, a keyboard 1210 or a touch panel device. The computer 2' may include two or more of each component.

In at least one embodiment, at least one computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 2, 2', communicates with one or more other system components (e.g., the medical device 1, the guidance device 105, the PACS 4, the CT scanner 5 or other type of scanner, of system 10 or other device or system being used for medical procedure (e.g., needle guidance, ablation, biopsy, visualization and manipulation of registration result(s), etc.) planning and/or performance) to perform imaging, planning and/or performance. The monitor or display 1209 displays the plan and performance and/or guidance steps (e.g., in real time), and may display other information about the imaging condition or about an object to be imaged and operated on during the procedure. The monitor 1209 also provides a graphical user interface for a user to operate an ablation planning and/or performance and/or needle guidance or ablation (or other medical procedure) probe guidance device or system (e.g., the system 10). An operation signal is input from the operation unit (e.g., such as, but not limited to, a mouse device 1211, a keyboard 1210, a touch panel device, etc.) into the operation interface 1214 in the computer 2', and corresponding to the operation signal the computer 2' instructs the system (e.g., the system 10) to set or change the imaging, planning and/or performance condition(s), and to start or end any portion of any of the method(s) discussed herein.

The present disclosure and/or one or more components of devices, systems and storage mediums, and/or methods, thereof also may be used in conjunction with any suitable optical assembly including, but not limited to, ablation technology, such as in U.S. Pat. No. 9,867,673; U.S. patent application Ser. Nos. 16/027,093, 15/836,141, and 15/727,978; U.S. Provisional Patent Application No. 62/764,849, filed on Aug. 15, 2018; U.S. Provisional Patent App. No. 62/764,820, filed Aug. 15, 2018; U.S. Provisional Patent App. No. 62/875,243, filed Jul. 17, 2019; U.S. patent application Ser. No. 16/539,769, filed Aug. 13, 2019; U.S. Pat. Pub. No. 2019/0105109, published on Apr. 11, 2019; U.S. Pat. Pub. No. 2019/0008591, published on Jan. 10, 2019; U.S. Pat. Pub. No. 2018/0098819, published on Apr. 12, 2018; App. No. PCT/US2018/020752; and App. No. PCT/US15/40336, each of which patent(s), patent publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A method of guiding and controlling at least one medical instrument or tool of a medical guidance device and/or performing registration using one or more masks, the medical guidance device comprising a first portion including a portion defining an opening; one or more fiducial markers that operate to be used to align, and confirm alignment of, the first portion on a patient via device-to-image registration of the medical guidance device; and a second movable portion that is rotatably mateable with the first portion, wherein the at least one medical instrument or tool operates to be inserted through an insertion point of a surface, the method comprising:

identifying at least three candidate fiducial markers in an image, the at least three candidate fiducial markers being located in a fiducial marker plane and the at least three candidate fiducial markers to be identified as three or more actual fiducial markers of the one or more fiducial markers of the medical guidance device;

masking at least the at least one medical instrument or tool and/or one or more portions of the medical guidance device other than the identified at least three candidate fiducial markers in the image using the one or more masks to suppress at least the at least one medical instrument or tool and/or the one or more portions of the medical guidance device other than the at least three candidate fiducial markers in the image, the image including an unmasked portion of the medical guidance device and including a region/area or target of interest including the at least three candidate fiducial markers;

identifying the three or more actual fiducial markers from the identified at least three candidate markers after the masking; and performing the device-to-image registration using the masked image or masked image information and using the three or more identified actual markers.

2. The method of claim 1, wherein the device-to-image registration includes performing automatic or manual registration of at least the medical guidance device using the one or more masks and improving quality of the image using the one or more masks for performing the automatic or manual device-to-image registration by making an object(s), region/area, or a target of interest in the image less obscure or enhancing the object(s), the region/area, or the target of interest in the image for improved resolution or image quality via defining or generating the less obscure or enhanced object(s), region/area, or target of interest in the image.

3. The method of claim 1, wherein the second movable portion is positioned to a predetermined position relative to the first portion, wherein the one or more fiducial markers are disposed in/on or within one of the mated first portion and the second movable portion, and wherein the at least one medical instrument or tool is positioned to or disposed at a predetermined position upon the second movable portion.

4. The method of claim 1, further comprising one or more of the following:

(i) matching a model or a device plane of known fiducial orientation with the image including the one or more fiducial markers of the medical guidance device;

(ii) using the at least three candidate fiducial markers to be identified as the actual fiducial markers of the one or more fiducial markers of the medical guidance device to define a model or a device plane of fiducial marker orientation;

(iii) matching one or more models or device planes of known fiducial orientation with the image including the one or more fiducial markers of the medical guidance device, and overlaying and/or registering the one or more models or device planes and the image; and/or (iv) using four or more fiducial markers of the one or more fiducial markers to define a fiducial plane for the four or more fiducial markers and to confirm that the fiducial plane for the four or more fiducial markers is accurate.

5. The method of claim 1, wherein:

(i) the method further comprises using the one or more fiducial markers to align, and confirm alignment of, the first portion on the patient in a targeted orientation or in a predetermined location via the device-to-image registration of the medical guidance device; and (ii) the second movable portion further includes:

a frame defining an opening that operates to overlay the opening of the first portion when the first portion and the second movable portion are mated with each other;

an arc member attached to the frame; and a holder slideably attached to the arc member, wherein the holder operates to hold the at least one medical instrument or tool to be guided by the medical guidance device.

6. The method of claim 1, wherein the second movable portion includes:

(i) a frame defining an opening that operates to overlay the opening of the first portion in a case where the first portion and the second movable portion are mated with each other such that the portion defining the opening of the first portion and the frame defining the opening of the second movable portion are substantially parallel or are parallel and/or such that a first side of the portion of the first portion is in direct contact with a first side of the frame of the second movable portion and a second side of the portion of the first portion is in direct contact with a second side of the frame of the second movable portion; and (ii) an arc member attached to the frame and extending from a first side of the second movable portion to a second side of the second movable portion, the arc member operating to hold the at least one medical instrument or tool to be guided by the medical guidance device, wherein the at least one medical instrument or tool is positioned to or disposed at a predetermined position upon the second movable portion.

7. The method of claim 1, further comprising:

in a case where the first portion and/or the medical guidance device is positioned on and/or fixed to the patient for performing a medical procedure with the at least one medical instrument or tool, calculating an orientation of the first portion and/or the medical guidance device to determine whether one or more registration results indicate that the first portion and/or the medical guidance device is positioned or fixed in a targeted orientation or in a predetermined location, wherein the targeted orientation or the predetermined location operates to be disposed or positioned on or above the patient.

8. The method of claim 1, further comprising:

acquiring and/or loading images and/or acquiring imaging data;

selecting a target point and an insertion point to plan an insertion of the at least one medical instrument or tool;

using the target point and the insertion point to create a proposed insertion line trajectory;

translating the insertion line trajectory from a pixel space to a patient space;

identifying one or more points at a set or predetermined parameterized distance from the insertion line trajectory;

translating the insertion line trajectory back from the patient space to the pixel space and assigning the identified one or more points a pixel value of one or a high pixel value to define the one or more masks;

placing and/or imaging the medical guidance device; and performing the device-to-image registration of at least the medical guidance device using the one or more masks, the device-to-image registration being automatic or manual, and/or improving the quality of the image using the one or more masks by making an object(s), the region/area, or the target of interest in the image less obscure or by enhancing the object(s), the region/area, or the target of interest in the image for improved resolution or image quality.

9. The method of claim 8, further comprising allowing or having a user of the medical guidance device adjust the one or more masks, and/or displaying a Graphical User Interface that operates to instruct, or allow, a user of the medical guidance device to enter input operating to adjust the one or more masks based on the input.

10. The method of claim 8, further comprising one or more of the following:

after translating the insertion line trajectory back from the patient space to the pixel space, determining whether to add another medical instrument(s) or tool(s), needle(s), or object(s) to the image;

in a case where it is determined to add another medical instrument(s) or tool(s), needle(s), or object(s) to the image, repeating the acquiring and/or loading, the selecting, the using, the translating from the pixel space to the patient space, the identifying points, the translating from the patient space to the pixel space, and the determining steps for each added, another medical instrument(s) or tool(s), needle(s), or object(s);

in a case where it is determined to not add another medical instrument(s) or tool(s), needle(s), or object(s) to the image, applying the one or more masks to one or more medical instruments or tools, needles, or objects other than the at least one medical instrument or tool, a target needle, or a target object for insertion; and/or selectively unmasking one or more desired medical instruments or tools, needles, or objects of the one or more medical instruments or tools, needles, or objects other than the at least one medical instrument or tool, the target needle, or the target object.

11. The method of claim 8, further comprising one or more of the following:

cropping the image;

allowing a user of the medical guidance device to modify the one or more masks interactively; and/or determining the insertion line trajectory based on one or more of the insertion point and the target point.

12. The method of claim 1, further comprising:

acquiring and/or loading images and/or acquiring imaging data;

selecting a target portion or a center of one or more of the one or more artifacts, needles, or objects in the image;

projecting a box or other geometrically-shaped indicator with predetermined or set parameterized values around the target portion or the center of the one or more of the one or more artifacts, needles, or objects in the image;

translating a proposed, determined or predetermined insertion line trajectory from a pixel space to a patient space;

identifying one or more points within the box or other geometrically-shaped indicator;

translating the insertion line trajectory back from the patient space to the pixel space and assigning the identified one or more points a pixel value of one or a high pixel value to define the one or more masks;

placing and/or imaging the medical guidance device; and performing the device-to-image registration of at least the medical guidance device using the one or more masks, the device-to-image registration being automatic or manual, and/or improving the quality of the image using the one or more masks by making an object(s), the region/area, or the target of interest in the image less obscure or by enhancing the object(s), the region/area, or the target of interest in the image for improved resolution or image quality.

13. The method of claim 1, further comprising overlaying a model fiducial plane having fiducials therein with the image having one or more of the one or more fiducial markers therein.

14. The method of claim 1, further comprising one or more of the following:

modifying the one or more masks based on at least one user interaction between the image being displayed on a display and a user of the medical guidance device such that the display operates to allow the user to enter one or more inputs that operate to modify the one or more masks;

modifying the one or more masks based on at least one user interaction between the image being displayed on a display and a user of the medical guidance device and based on one or more specifications of the at least one medical instrument or tool, a needle, an object, an artifact in the image, and/or the one or more portions of the medical guidance device other than the identified at least three candidate fiducial markers; and/or based on at least one user interaction between the image being displayed on a display and a user of the medical guidance device, performing one or more of the following processes as the at least one user interaction: changing a width of the at least one medical instrument or tool, a needle, or an object(s) to be masked; changing a height of the at least one medical instrument or tool, the needle, or the object(s) to be masked; changing a depth of the at least one medical instrument or tool, the needle, or the object(s) to be masked; and defining a size or shape of one or more masks of the one or more masks based on one or more specifications of the at least one medical instrument or tool, the needle, the object(s), and/or the one or more portions of the medical guidance device other than the identified at least three candidate fiducial markers.

15. The method of claim 1, further comprising one or more of the following:

(i) based on at least one user interaction between the image being displayed on a display and a user of the medical guidance device, allowing a user to visualize and manipulate the device-to-image registration result(s) to mask or unmask and update one or more of the one or more fiducial markers, one or more locations of artifacts, one or more objects, or one or more regions of interest in the image;

(ii) based on at least one user interaction between the image being displayed on a display and a user of the medical guidance device and based on masked or unmasked and updated one or more fiducial markers, one or more locations of artifacts, one or more objects, or one or more regions of interest in the image, performing automatic device-to-image registration of the medical guidance device;

(iii) based on at least one user interaction between the image being displayed on a display and a user of the medical guidance device, allowing the user to view unmasked or masked and updated one or more fiducial markers, one or more locations of artifacts, one or more objects, or one or more regions of interest in the image, and analyzing a re-calculated device-to-image registration of the medical guidance device and/or any remaining registration error; and/or (iv) based on at least one user interaction between the image being displayed on a display and a user of the medical guidance device, providing the user with immediate feedback on how a mask change affects the device-to-image registration to improve or optimize the device-to-image registration.

16. A non-transitory storage medium storing at least one program to be executed by a processor to perform a method for guiding and controlling at least one medical instrument or tool of a medical guidance device and/or performing registration using one or more masks, the medical guidance device comprising a first portion including a portion defining an opening; one or more fiducial markers that operate to be used to align, and confirm alignment of, the first portion on a patient via device-to-image registration of the medical guidance device; and a second movable portion that is rotatably mateable with the first portion, wherein the at least one medical instrument or tool operates to be inserted through an insertion point of a surface, the method comprising:

identifying at least three candidate fiducial markers in an image, the at least three candidate fiducial markers being located in a fiducial marker plane and the at least three candidate fiducial markers to be identified as three or more actual fiducial markers of the one or more fiducial markers of the medical guidance device;

masking at least the at least one medical instrument or tool and/or one or more portions of the medical guidance device other than the identified at least three candidate fiducial markers in the image using the one or more masks to suppress at least the at least one medical instrument or tool and/or the one or more portions of the medical guidance device other than the at least three candidate fiducial markers in the image, the image including an unmasked portion of the medical guidance device and including a less obscure or enhanced region/area or target of interest including the at least three candidate fiducial markers;

identifying the three or more actual fiducial markers from the identified at least three candidate markers after the masking; and performing the device-to-image registration using the masked image or masked image information and using the three or more identified actual markers.

* * * * *